US009102981B2

(12) United States Patent
Perreault et al.

(10) Patent No.: US 9,102,981 B2
(45) Date of Patent: Aug. 11, 2015

(54) ASSESSMENT AND REDUCTION OF RISK OF GRAFT-VERSUS-HOST DISEASE

(71) Applicants: Université de Montréal, Montreal (CA); Biosystemix Ltd., Kingston (CA)

(72) Inventors: Claude Perreault, Outremont (CA); Chantal Baron, Montreal (CA); Roland Somogyi, Sydenham (CA); Larry D. Greller, Annapolis, MD (US)

(73) Assignees: VALORISATION-RECHERCHE, LIMITED PARTNERSHIP, Montreal (CA); RSEM, LIMITED PARTNERSHIP, Montreal (CA)

( * ) Notice: Subject to any disclaimer, the term of this patent is extended or adjusted under 35 U.S.C. 154(b) by 45 days.

(21) Appl. No.: 13/682,303

(22) Filed: Nov. 20, 2012

(65) Prior Publication Data

US 2013/0324427 A1    Dec. 5, 2013

Related U.S. Application Data

(60) Continuation of application No. 12/814,271, filed on Jun. 11, 2010, now abandoned, which is a division of application No. 11/741,492, filed on Apr. 27, 2007, now Pat. No. 7,763,425.

(60) Provisional application No. 60/745,761, filed on Apr. 27, 2006.

(51) Int. Cl.
    C12Q 1/68       (2006.01)
    C12P 19/34      (2006.01)
    C07H 21/04      (2006.01)
    A61K 35/26      (2006.01)
    G01N 33/68      (2006.01)

(52) U.S. Cl.
    CPC .......... *C12Q 1/6876* (2013.01); *C12Q 1/6881* (2013.01); *C12Q 1/6883* (2013.01); *G01N 33/6863* (2013.01); C12Q 2600/158 (2013.01); G01N 2800/245 (2013.01)

(58) Field of Classification Search
    None
    See application file for complete search history.

(56) References Cited

FOREIGN PATENT DOCUMENTS

WO    WO 02/057414      7/2002
WO    WO 2004/042346    5/2004
WO    WO 2005/074540    8/2005

OTHER PUBLICATIONS

Shulzhenko (Human Immunology 2001 vol. 62 pp. 342-347).*
Lee (International Immunology 2004 vol. 16 No. 8 pp. 1109-1124).*
Flechner (American Journal of Transplantation 2004 vol. 4 pp. 1475-1489).*
Chan, Eric. Integrating Transcriptomics and Proteomics. G&P magazine 2006 vol. 6 No. 3 pp. 20-26.*
Form PCT/ISA/220, 237 and 210 from PCT Application No. PCT/CA2007/000714.
Allison et al. "Microarray data analysis: from disarray to consolidation and consensus." *Nature Reviews*. vol. 7. 2006. pp. 55-65.
Anderson et al. "Distinct roles for donor- and host-derived antigen-presenting cells and costimulatory molecules in murine chronic graft-versus-host disease: requirements depend on target organ." *Blood* vol. 105. 2005. pp. 2227-2234.
Antin et al. "Establishment of Complete and Mixed Donor Chimerism after Allogeneic Lymphohematopoietic Transplantation: Recommendations from a workshop at 2001 Tandem Meetings." *Biology of Blood and Marrow Transplantation* vol. 7. 2001. pp. 473-485.
Aplan et al. "Structural Characterization of *SIL*, a Gene Frequently Disrupted in T-Cell Acute Lymphoblastic Leukemia." *Molecular and Cellular Biology*. vol. 11, No. 11. 1991. pp. 5462-5469.
Banovic et al. "TFG-β in allogeneic stem cell transplantation: friend or foe?" *Blood*. vol. 106. No. 6. 2005. pp. 2206-2214.
Baranzini et al. Transcription-Based Prediction of Reponse to IFNβ Using Supervised Computational Methods. *PLOS Biology*. vol. 3, No. 1. 2005. pp. 166-176.
Go et al. "NFAT/TonEBP mutant mice define osmotic stress as a critical feature of the lymphoid microenvironment." *PNAS*. vol. 101. No. 29. 2004. pp. 10673-10678.
Hakim et al. "Age-dependent incidence, time course, and consequences of thymic renewal in adults." *The Journal of Clinical Investigation*. vol. 115, No. 4. 2005. pp. 930-939.
Jung et al. "Homeotic factor ATBF1 induces the cell cycle arrest associated with neuronal differentiation."*Development*. vol. 132. No. 23. 2005. pp. 5137-5145.
Kumamoto et al. "Monoclonal Antibody Specific for TIRC7 Induces Donor-specific Anergy and Prevents Rejection of Cardiac Allografts in Mice." *American Journal of Transplantation*. vol. 4. 2004. pp. 505-514.
Lee et al. "A Survey of Diagnosis, Management, and Grading of Chronic GVHD." *Biology of Blood Marrow Transplantation*. vol. 8. 2002. pp. 32-39.
Leisenring et al. "An acute graft-versus-host disease activity index to predict survival after hematopoietic cell transplantation with myeloablative conditioning regimens." *Blood*. vol. 108. 2006. pp. 749-755.
Li et al. "CD24 Expression on T Cells Is Required for Optimal T Cell Proliferation in Lymphopenic host." *The Journal of Experimental Medicine*. vol. 200. No. 8. 2004. pp. 1083-1089.
Perreault et al. "Minor Histocompatibility Antigens." *Blood*. vol. 76. No. 7. 1990. pp. 1269-1280.
Soubeyran et al. "Cbl-CIN85-endophiln complex mediated ligand-induced downregulation of EGF receptors." *Nature*. vol. 416. 2002. pp. 183-187.
Utku et al. "Prevention of Acute Allograft Rejection by Antibody Targeting of TIRC7, a Novel T Cell Membrane Protein." *Immunity*. vol. 9. 1998. pp. 509-518.

(Continued)

Primary Examiner — Amanda Haney
(74) Attorney, Agent, or Firm — Merchant & Gould P.C.

(57) ABSTRACT

Methods of assessing and reducing risk of graft versus host disease (GVHD) based on gene expression profiling are described, as well as methods of selecting a suitable transplant donor. Corresponding reagents and kits are also described.

21 Claims, 7 Drawing Sheets

(56) References Cited

OTHER PUBLICATIONS

Yau, P., "Microarray production: Implementing automation," *3rd Annual Ontario Microarray Symposium* Nov. 13, 2003. XP002540589.

Baron et al., "Prediction of graft-versus-host disease in humans by donor gene-expression profiling," *Plos Medicine* (2007) 4 (1): 69-83. XP002540588.

Supplementary European Search Report for EP 07 71 9640 mailed Sep. 9, 2009.

Chan, E., "Integrating transcriptomics and proteomics," *Genomics and Proteomics* (2006). Available online from www.genpromag.com, pp. 1/6.

Roman-Roman et al., "Identification of genes regulated during osteoblastic differentiation by genome wide expression analysis of mouse calvaria primary osteoblasts in vitro," *Bone* (2003) 32: 474-482.

Utku et al. "TIRC7 Deficiency causes In Vitro and In Vivo Augmentation of T and B Cell Activation and Cytokine Response." *The Journal of Immunology*. vol. 173. 2004. pp. 2342-2352.

Vogelsang et al. "Pathogenesis and Treatment of Graft-Versus-Host Disease after bone marrow transplant." *Annu. Rev. Med.* vol. 54. 2003. pp. 29-52.

Whitney et al. "Individuality and variation in gene expression patterns in human blood." *PNAS* vol. 100. No. 4. 2003. pp. 1896-1901.

Woodgett et al. "Recent advances in the protein kinase B signaling pathway." *Current Opinion in Cell Biology*. vol. 17. 2005. pp. 150-157.

Wright et al. "Characterization of Mice Lacking the Tetraspanin Superfamily Member CDI51." *Molecular and Cellular Biology*. vol. 24. No. 13. 2004. pp. 5978-5988.

Affymetrix web site: https://www.affymetrix.com/analysis/netaffx/fullrecord.affx?pk=HG-U133A:204158_S_AT accessed Jul. 18, 2012.

Lee, Myeong Sup et al., "Gene expression profiles during human CD4+ T cell differentiation" International Immunology 2004 vol. 16 No. 8 pp. 1109-1124.

\* cited by examiner

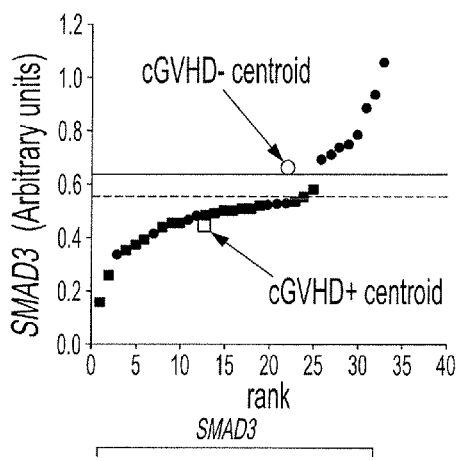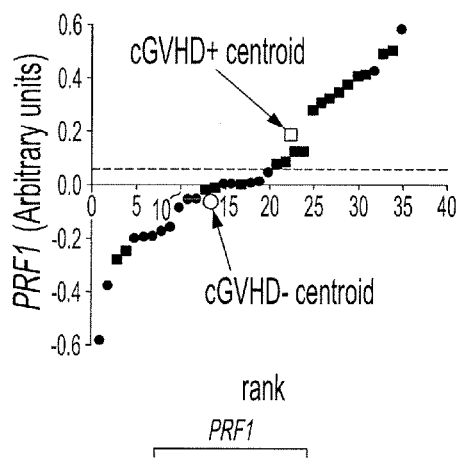
Fig. 3A                    Fig. 3B

ASSESSMENT AND REDUCTION OF RISK OF GRAFT-VERSUS-HOST DISEASE

CROSS REFERENCE TO RELATED APPLICATIONS

This application is a Continuation application of U.S. application Ser. No. 12/814,271, filed Jun. 11, 2010, which is a Divisional application of U.S. application Ser. No. 11/741,492, filed Apr. 27, 2007, which claims the benefit, under 35 U.S.C. §119(e), of U.S. provisional application Ser. No. 60/745,761 filed Apr. 27, 2006 and which application(s) are incorporated herein by reference. A claim of priority to all, to the extent appropriate is made.

FIELD OF THE INVENTION

The invention relates to assessing and reducing the risk of graft-versus-host disease (GVHD) and more particularly relates to assessing risk of a potential transplant donor of inducing GVHD in a transplant recipient, which may in turn allow the selection of a donor exhibiting reduced risk.

BACKGROUND OF THE INVENTION

For dysfunctional and/or diseased organs or cells of the body, besides therapeutic intervention with drugs, organ or cell transplantation is an alternative, sometimes the last resort in the treatment of the patient. Particularly for patients with leukemia, end-stage renal, cardiac, pulmonary or hepatic failure, transplantation is quite commonly used in treatment. For example, allografts (organ grafts harvested from donors other than the patient him/herself or host/recipient of the graft) of various types, e.g., kidney, heart, lung, liver, bone marrow, pancreas, cornea, small intestine and skin (e.g., epidermal sheets) are currently routinely performed. Xenografts (organ grafts harvested from another species, e.g. non-human animal donors in the case of human recipients), such as porcine heart valves, are also being used clinically to replace their dysfunctional human counterparts. To ensure successful transplantation, it is desirable to obtain the graft from the patient's identical twin or his/her immediate family member to increase histocompatibility (compatibility of genetically defined cellular markers that may be recognized as foreign and attacked by the immune system if mismatched). This is because transplants evoke a variety of immune responses in the host, which results in rejection of the graft by the host immune system, or graft-versus-host disease (hereinafter, referred to as "GVHD") in which the transplanted immune system cells (bone marrow or hematopoietic cell transplants) cause an attack of host tissues and related and often severe complications.

Bone marrow and/or stem cell transplantation has applications in a wide variety of clinical settings, including solid organ transplantation. A major goal in solid organ transplantation is the engraftment of the donor organ without a graft rejection immune response generated by the recipient, while preserving the immunocompetence of the recipient against other foreign antigens. Typically, nonspecific immunosuppressive agents such as cyclosporin A, azathioprine, corticosteroids including prednisone, and methylprednisolone, cyclophosphamide, and FK506 are used to prevent host rejection responses (Iwasaki, (2004). Clinical Medicine & Research 2(4): 243). They must be administered on a daily basis and if stopped, graft rejection usually results. However, nonspecific immunosuppressive agents function by suppressing all aspects of the immune response, thereby greatly increasing a recipient's susceptibility to infections and diseases, including cancer. Furthermore, although the development of new immunosuppressive drugs has led to an improvement in the survival of patients, these drugs are associated with a high incidence of side effects such as nephrotoxicity and/or hepatotoxicity.

The goal of hematopoietic progenitor cell or stem cell transplantation is to achieve the successful engraftment of donor cells within a recipient host, such that immune and/or hematopoietic chimerism results. Chimerism is the reconstitution of the various compartments of the recipient's hematoimmune system with donor cell populations bearing major histocompatibility complex (MHC) molecules derived from both, the allogeneic or xenogeneic donor, and a cell population derived from the recipient or, alternatively, the recipient's hematoimmune system compartments which can be reconstituted with a cell population bearing MHC molecules derived from only the allogeneic or xenogeneic marrow donor. Chimerism may vary from 100% (total replacement by allogenic or xenogeneic cells) to low levels detectable only by molecular methods. Chimerism levels may vary over time and be permanent or temporary.

GVHD is a possible severe or lethal complication of any hematopoietic cell transplant that uses stem cells from either a related or an unrelated donor, which occurs in about 35-50% of recipients of untreated HLA (human leukocyte histocompatibility antigens)-identical marrow grafts (Martin et al., (1985). Blood 66:664-72) and up to 80% of recipients of HLA-mismatched marrow. Such transplants typically are used in the treatment of disorders such as leukemia, bone marrow failure syndromes, and inherited disorders (e.g., sickle cell anemia, thalassemia, immunodeficiency disorders, and metabolic storage diseases such as mucopolysaccharidosis), as well as low-grade lymphoma. GVHD arises from a reaction of donor T cells (T lymphocytes) against MHC or minor histocompatibility antigen disparities present on antigen-presenting cells (APC) and various tissues of the individual receiving the donor cells (Schlomchik et al., (1999). Science 285:412-5). GVHD can be exacerbated by tissue injury induced by pre-bone marrow transplant conditioning that includes destruction of the recipient's bone marrow. Acute GVHD (aGVHD) usually occurs within the first three months following a transplant, and can affect the skin, liver, stomach, and/or intestines. Chronic GVHD (cGVHD) is the late form of the disease, and usually develops three months or more after a transplant. The symptoms of cGVHD resemble spontaneously occurring autoimmune disorders such as lupus or scleroderma (Iwasaki, supra).

Therefore, graft rejection still remains a major source of morbidity and mortality in human transplantation and there still exists the need for controlling, reducing, and treating GVHD.

The present description refers to a number of documents, the content of which is herein incorporated by reference in their entirety.

SUMMARY OF THE INVENTION

The invention relates to methods, uses, and corresponding products (e.g. probes, collections, kits, etc.) for the assessment of risk of graft versus host disease (GVHD), as well as corresponding diagnostic and therapeutic methods, uses, products and kits associated with such risk assessment.

In a first aspect, the present invention relates to a method of assessing risk, of a candidate transplant donor, of inducing graft versus host disease (GVHD) in a transplant recipient, said method comprising:

(a) comparing a candidate gene expression profile derived from a biological sample from said candidate transplant donor to a corresponding reference gene expression profile, wherein said candidate gene expression profile comprises a candidate expression value for one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CK52, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI;
wherein said reference gene expression profile comprises a reference expression value for said one or more gene(s), said reference expression profile being derived from a comparison of:
  (i) a GVHD+ expression profile comprising a GVHD+ expression value for one or more gene(s) derived from a biological sample obtained from a transplant donor known to have induced GVHD in a transplant recipient with
  (ii) a GVHD− expression profile comprising a GVHD− expression value for one or more gene(s) derived from a biological sample obtained from a transplant donor known to have not induced GVHD in a transplant recipient,
whereby said reference expression value is determined as being the level of expression midway between said GVHD+ and GVHD− expression values whereby said midway level separates a GVHD+ class comprising said GVHD+ expression value from a GVHD− class comprising said GVHD− expression value; the level of expression between said GVHD+ and GVHD− expression values defined as separating expression values into GVHD+ and GVHD− classes on the basis of discriminatory analysis; or both; and
  (b) assessing risk of said candidate transplant donor of inducing graft versus host disease (GVHD) in a transplant recipient in accordance with said comparison of said candidate gene expression profile with said reference gene expression profile.

In an embodiment, the expression value of the above-mentioned gene(s) is determined by determining the level of expression of one or more nucleic acid(s) or polypeptide(s) encoded thereby comprising a sequence selected from SEQ ID NOs: 1-206

In an embodiment, a candidate expression value within said GVHD+ class is indicative that said candidate transplant donor has an increased risk of inducing GVHD in a transplant recipient.

In another embodiment, a candidate expression value within said GVHD− class is indicative that said candidate transplant donor has a reduced/decreased risk of inducing GVHD in a transplant recipient.

In an embodiment, the above-mentioned one or more gene(s) is selected from TCIRG1, SMAD3, ATBF1, AKT2, CD24, CD151, TGIF, SIL, PRF1, FNBP3, TGFBI, EP300, SH3KBP1, NMI, FURIN and NFAT5. In a further embodiment, the expression value of the above-mentioned one or more gene(s) is determined by determining the level of expression of a nucleic acid or polypeptide encoded thereby comprising a sequence selected from SEQ ID NOs: 7-8, 45-46, 99-104, 107-108, 113-114, 119-120, 139-140, 151-156, 183-184, 189-190 and 203-206.

In another embodiment, the above-mentioned one or more gene(s) is selected from SH3KBP1, PRF1, CD151, EP300, FNBP3, NMI, SIL, TCIRG1, NFAT5, AKT2, FURIN, ATBF1, SMAD3, CD24, TGIF and TGFBI.

In yet another embodiment, the above-mentioned one or more gene(s) is one or more gene pair(s) selected from the group consisting of (a) SH3KBP1 and NFAT5; (b) PRF1 and NFAT5; (c) PRF1 and TCIRG1; and (d) CD151 and SIL.

In another embodiment, the above-mentioned reference gene expression profile is contained within a database.

In another embodiment, the above-mentioned comparing is carried out using a computer algorithm.

In another embodiment, the above-mentioned method comprises determining the expression value of at least 2 genes, in another embodiment the expression value of at least 5 genes, in yet another embodiment the expression value of at least 10 genes.

In an embodiment, the above-mentioned biological sample is a CD4$^+$ T cell and the above-mentioned one or more gene(s) is selected from RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, RFXANK, SMAD3, VIM, CDC25B, TGIF and TGFBI. In a further embodiment, the above-mentioned one or more gene(s) is selected from TCIRG1, SMAD3, ATBF1, AKT2, CD151, SIL, FNBP3, EP300, NMI, FURIN, TGIF and TGFBI.

In another embodiment, the above-mentioned biological sample is a CD8$^+$ T cell and the above-mentioned one or more gene(s) is selected from CD3D, CD1A, IL15RA, IL2RG, ILF1, LAT, MGMT, TLR1, RGS13, THBS1, TCIRG1, PIAS4, NFAT5, BAG3, VEGF, YY1, FURIN, CCND1, CHERP, CSDA, DOK2, FOXJ1, MCAM, NFKB2, PTGER4, DAD1, ILF3, RFXANK, SMAD3, TNFRSF1B, VIM, CD24, DAP, HLA-DRB1, HSPB1, PRKACA, HDAC5 and CDC25B. In a further embodiment, the above-mentioned one or more gene(s) is selected from CD24, NFAT5 and TCIRG1.

In an embodiment, the above-mentioned biological sample is a CD4$^+$ T cell and the above-mentioned one or more gene(s) is selected from CD151, EP300, FNBP3, NMI, SIL, TCIRG1, AKT2, FURIN, ATBF1, SMAD3, TGIF and TGFBI.

In another embodiment, the above-mentioned biological sample is a CD8$^+$ T cell and the above-mentioned one or more gene pair(s) is selected from the group consisting of (a) SH3KBP1 and NFAT5; (b) PRF1 and NFAT5; and (c) PRF1 and TCIRG1.

In an embodiment, the above-mentioned biological sample is a CD4$^+$ T cell and the above-mentioned one or more gene(s) is selected from CXCR6, SMAD1, FAF1, BCAP31, RANBP2, SNRPN, SOCS5, ANXA5, CD63, CD81, CK52, CPE, MAD, MYCL1, PDCD8, RHOA, SKP2 and YWHAQ.

In another embodiment, the above-mentioned biological sample is a CD8$^+$ T cell and said one or more gene(s) is selected from FAF1, SH3KBP1, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, SOCS5, ANXA5, CD81, CK52, MYCL1, SKP2, YWHAQ, GAPD, PPIE and RAN. In a further embodiment, the above-mentioned one or more gene(s) is PRF1 and/or SH3KBP1.

In an embodiment, the above-mentioned one or more gene(s) is selected from SMAD3, TGIF, PRF1, FNBP3, TGFBI, EP300 and FURIN. In a further embodiment, the expression value of the above-mentioned one or more gene(s) is determined by determining the level of expression of a nucleic acid or polypeptide encoded thereby comprising a sequence selected from SEQ ID NOs: 45-46, 101-104, 153-154, 183-184 and 203-206.

In an embodiment, the above-mentioned biological sample is a CD4$^+$ T cell and the above-mentioned one or more gene(s) is selected from SMAD3, TGIF, FNBP3, TGFBI, EP300 and FURIN.

In another embodiment, the above-mentioned biological sample is a CD4$^+$ T cell and wherein said one or more gene(s) is PRF1.

In an embodiment, the above-mentioned expression value is determined at the nucleic acid level. In a further embodiment, the above-mentioned nucleic acid is messenger RNA (mRNA).

In another embodiment, the above-mentioned expression value is determined using a technique selected from the group consisting of Northern blot analysis, reverse transcription PCR, real time quantitative PCR, microarray analysis and RNase protection.

In an embodiment, the above-mentioned expression value is determined at the polypeptide level. In a further embodiment, the above-mentioned level of polypeptide is determined using a reagent which specifically binds with the polypeptide. In a further embodiment, the above-mentioned reagent is an antibody or an antigen binding fragment thereof.

In an embodiment, the above-mentioned level of polypeptide is determined using a method selected from the group consisting of Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry and antibody microarray.

In another aspect, the present invention provides a collection of two or more isolated nucleic acids encoding one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI, their complements, or portions thereof.

In another aspect, the present invention provides a collection of two or more isolated nucleic acids, their complements, or portions thereof, wherein said nucleic acids comprise a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203 and 205.

In an embodiment, the above-mentioned collection comprises at least 5 isolated nucleic acids comprising a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203 and 205.

In an embodiment, the above-mentioned collection comprises at least 10 isolated nucleic acids comprising a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203 and 205.

In an embodiment, the above-mentioned collection comprises at least 25 isolated nucleic acids comprising a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203 and 205.

In an embodiment, the above-mentioned collection comprises at least 50 isolated nucleic acids comprising a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203 and 205.

In an embodiment, the above-mentioned collection comprises isolated nucleic acids comprising all nucleic acid sequences selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203 and 205.

In an embodiment, the above-mentioned isolated nucleic acids are conjugated to a detectable marker.

In an embodiment, the above-mentioned isolated nucleic acids are hybridizable array elements in a microarray.

In another aspect, the present invention provides a kit comprising the above-mentioned collection together with instructions setting forth the above-mentioned method of assessing risk.

In another embodiment, the above-mentioned biological sample is selected from a cell, a tissue and a body fluid. In a further embodiment, the above-mentioned cell is a Peripheral Blood Mononuclear Cell (PBMC). In a further embodiment, the above-mentioned cell is selected from a $CD4^+$ and a $CD8^+$ T cell.

In an embodiment, the above-mentioned kit further comprises a data analysis tool. In a further embodiment, the above-mentioned data analysis tool is a computer program. In another embodiment, the above-mentioned data analysis tool comprises an algorithm adapted to discriminate between gene expression profiles associated with increased and reduced risks of inducing GVHD in a transplant recipient.

In another aspect, the present invention provides a method of selecting a transplant donor so as to reduce the risk of inducing GVHD in a recipient, said method comprising:
 (a) performing the above-mentioned method of assessing risk; and
 (b) selecting said donor in accordance with said risk assessment.

In another aspect, the present invention provides an in vitro method of selecting a transplant donor so as to reduce the risk of inducing GVHD in a recipient, said method comprising:
 (a) performing the above-mentioned method of assessing risk; and
 (b) selecting said donor in accordance with said risk assessment.

In an embodiment, the above-mentioned expression value is obtained by determining the level of expression of a nucleic acid or polypeptide encoded thereby comprising a sequence selected from SEQ ID NOs: 1-206.

In another aspect, the present invention provides a use of the above-mentioned collection or the above-mentioned kit for assessing risk, of a candidate transplant donor, of inducing graft versus host disease (GVHD) in a transplant recipient.

In another aspect, the present invention provides a GVHD risk assessment expression profile map comprising gene expression level information for one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI.

In an embodiment, the above-mentioned map is digital information stored in a computer-readable medium.

In another embodiment, the above-mentioned computer readable medium further comprises the above-mentioned data analysis tool.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

(FIG. 2A) Number of genes showing a GVHD-predictive accuracy ≥65% and a p-value≤0.05. (FIG. 2B, FIG. 2C) Data from the H19K and ImmunArray were pooled. Among GVHD-predictive genes, Venn diagrams represent counts relationships between aGVHD- vs. cGVHD-predictive genes and $CD4^+$ vs. $CD8^+$ T cell gene profiles. In FIG. 2B: left=predictive in aGVHD; right=predictive in cGVHD, center=predictive in aGVHD and cGVHD. In FIG. 2C: left=predictive in $CD4^+$; right=predictive in $CD8^+$, center=predictive in $CD4^+$ and $CD8^+$.

FIGS. 3A-3B: LDA-based scatterplot of qRT-PCR data for SMAD3 and PRF1. Levels of SMAD3 and PRF1 transcripts were assessed in $CD4^+$ and $CD8^+$ T cells, respectively. Data for all donors tested by qRT-PCR were ranked according to relative gene expression levels. Thick horizontal dotted black line corresponds to the LDA (Linear Discriminant Analysis) separatrix (line separating groups of samples from different classes). For SMAD3, a computationally repositioned separatrix for 100% GVHD+ discrimination is shown (solid line in FIG. 3A).

(FIG. 4A) PIA (Predictive Interaction Analysis) identified four gene pairs whose p-value for cGVHD prediction was at least ten-fold lower (i.e., better) than that of the constituent genes. LDA-based scatterplots of qRT-PCR data for (FIG. 4B) NFAT5, (FIG. 4C) SH3KBP1, and (FIG. 4D) the NFAT5/SH3KBP1 gene pair. Dotted lines represent LDA-generated separatrices. Solid lines correspond to 100% cGVHD+ separatrices (designed to maximize sensitivity).

DESCRIPTION OF ILLUSTRATIVE EMBODIMENTS

Figure 1:
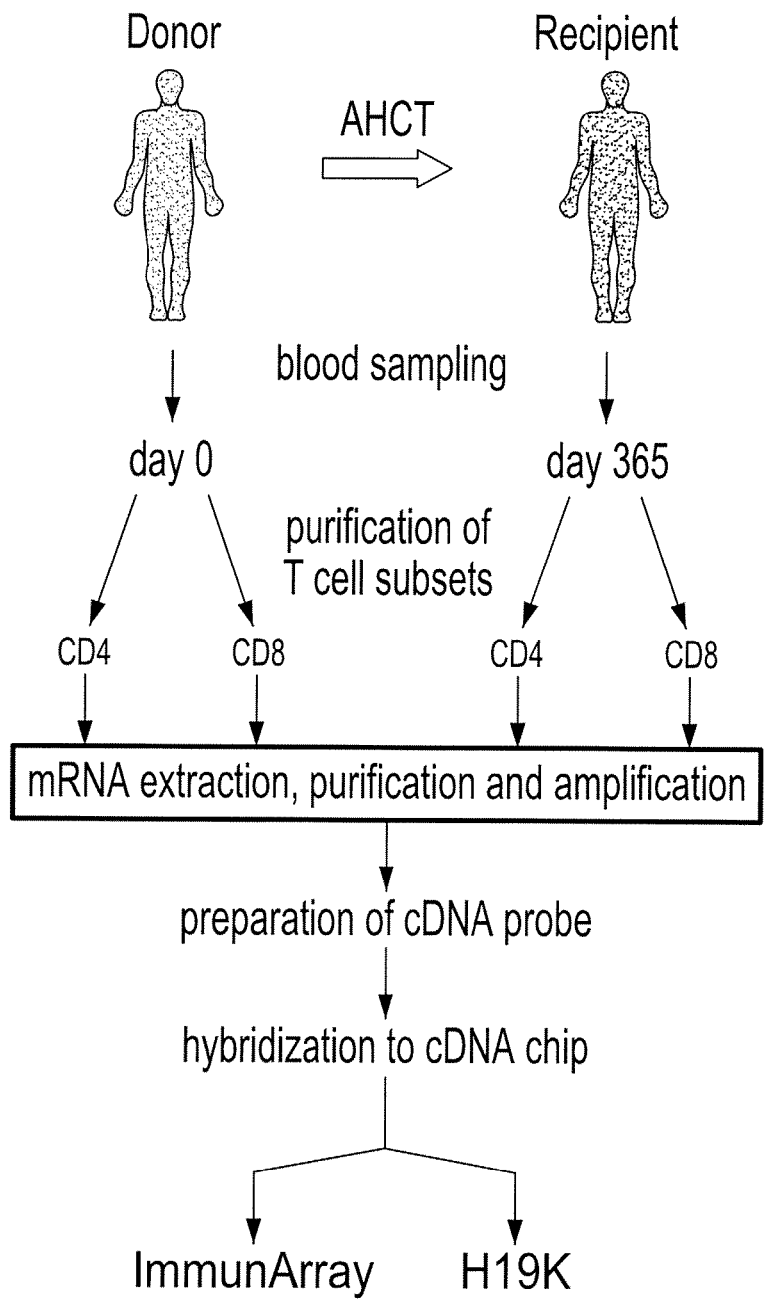
FIG. 1: Study design. Donor and recipient T cells were obtained on day 0 and 365, respectively. Total RNA from purified $CD4^+$ and $CD8^+$ T cells was reversed transcribed and hybridized on the human H19K array (donor and recipient T cells) and the ImmunArray™ (donor T cells) from The Microarray Centre of The Toronto University Health Network.

In the studies described herein, the gene expression profile of CD4$^+$ and CD8$^+$ T cells from AHCT (allogenic hematopoietic cell transplantation) donors was analyzed. It was found that pre-AHCT gene expression profiling segregates donors whose recipient suffered from GVHD or not. The "dangerous donor" trait (GVHD$^+$ recipient) is controlled and shaped by the activity of genes that regulate diverse cell functions.

Accordingly, in a first aspect, the present invention relates to a method of assessing risk, of a candidate transplant donor, of inducing graft versus host disease (GVHD) in a transplant recipient, said method comprising:

(a) comparing a candidate gene expression profile derived from a biological sample from said candidate transplant donor to a corresponding reference gene expression profile, wherein said candidate gene expression profile comprises a candidate expression value for one or more gene(s) selected from the group consisting of CXCR6 (chemokine (C-X-C motif) receptor 6), SMAD1 (SMAD, mothers against DPP homolog 1 (Drosophila)), FAF1 (Fas-associated factor 1), SH3KBP1 (SH3-domain kinase binding protein 1), HDAC2 (histone deacetylase 2), IL1R1 (interleukin 1 receptor, type I), CDC42 (cell division cycle 42), GADD45G (growth arrest and DNA-damage-inducible, gamma), IFNAR2 (interferon (alpha, beta and omega) receptor 2), IFRD1 (interferon-related developmental regulator 1), IGFBP2 (insulin-like growth factor binding protein 2), IRF3 (interferon regulatory factor 3), LIG4 (ligase IV, DNA, ATP-dependent), MAP2K1 (mitogen-activated protein kinase 1), MME (membrane metallo-endopeptidase), RASGRP1 (RAS guanyl releasing protein 1), STAT1 (signal transducer and activator of transcription 1), TFRC (transferrin receptor (p90, CD71)), TRIM22 (tripartite motif-containing 22), TFAP2C (transcription factor AP-2 gamma), CDC25A (cell division cycle 25 homolog A), GSR (glutathione reductase), PRF1 (perforin 1), BCAP31 (B-cell receptor-associated protein 31), RANBP2 (RAN binding protein 2), SNRPN (small nuclear ribonucleoprotein polypeptide N), SOCS5 (suppressor of cytokine signaling 5), ANXA5 (annexin A5), CD63 (CD63 molecule), CD81 (CD81 molecule), CKS2 (CDC28 protein kinase regulatory subunit 2), CPE (carboxypeptidase E), MAD (SMAD family member 2), MYCL1 (v-myc myelocytomatosis viral oncogene homolog 1, lung carcinoma derived), PDCD8 (programmed cell death 8; apoptosis-inducing factor, mitochondrion-associated, 1), RHOA (ras homolog gene family, member A), SKP2 (S-phase kinase-associated protein 2 (p45)), YWHAQ (tyrosine 3-monooxygenase/tryptophan 5-monooxygenase activation protein, theta polypeptide), GAPD (glyceraldehyde-3-phosphate dehydrogenase), PPIE (peptidylprolyl isomerase E (cyclophilin E)), RAN (RAN, member RAS oncogene family), FOSB (FBJ murine osteosarcoma viral oncogene homolog B), MAP2K6 (mitogen-activated protein kinase 6), SERPINB2 (serpin peptidase inhibitor, clade B (ovalbumin), member 2), TLR4 (toll-like receptor 4), CD3D (CD3d molecule, delta (CD3-TCR complex)), GAB2 (GRB2-associated binding protein 2), MAPK8IP1 (mitogen-activated protein kinase 8 interacting protein 1), SMO (smoothened homolog (Drosophila)), CD151 (CD151 molecule (Raph blood group)), EP300 (EP300 interacting inhibitor of differentiation 1), FNBP3 (PRP40 pre-mRNA processing factor 40 homolog A (S. cerevisiae)), IL6R (interleukin 6 receptor), NMI (N-myc (and STAT) interactor), PDK2 (pyruvate dehydrogenase kinase, isozyme 2), PPP1R16B (protein phosphatase 1, regulatory (inhibitor) subunit 16B), SIL (SCL/TAL1 interrupting locus; STIL), SNRP70 (small nuclear ribonucleoprotein 70 kDa polypeptide), STK38 (serine/threonine kinase 38), TCIRG1 (T-cell, immune regulator 1, ATPase, H+ transporting, lysosomal V0 subunit A3), CD1A (CD1a molecule), IL15RA (interleukin 15 receptor, alpha), IL2RG (interleukin 2 receptor, gamma), ILF1 (forkhead box K2; FOXK2), LAT (linker for activation of T cells), MGMT (O-6-methylguanine-DNA methyltransferase), TLR1 (toll-like receptor 1), RGS13 (regulator of G-protein signalling 13), THBS1 (thrombospondin 1), NFAT5 (nuclear factor of activated T-cells 5, tonicity-responsive), PIAS4 (protein inhibitor of activated STAT, 4), ADD1 (adducin 1 (alpha)), BAG3 (BCL2-associated athanogene 3), VEGF (vascular endothelial growth factor A), YY1 (YY1 transcription factor), AKT2 (v-akt murine thymoma viral oncogene homolog 2), FURIN (furin (paired basic amino acid cleaving enzyme)), ATBF1 (AT-binding transcription factor 1), CCND1 (cyclin D1), CHERP (calcium homeostasis endoplasmic reticulum protein), CSDA (cold shock domain protein A), DOK2 (docking protein 2, 56 kDa), FOXJ1 (forkhead box J1), HEXA (hexosaminidase A (alpha polypeptide)), LAMP2 (lysosomal-associated membrane protein 2), MCAM (melanoma cell adhesion molecule), NFKB2 (nuclear factor of kappa light polypeptide gene enhancer in B-cells 2 (p49/p100)), PTGER4 (prostaglandin E receptor 4 (subtype EP4)), DAD1 (defender against cell death 1), ILF3 (interleukin enhancer binding factor 3, 90 kDa), RFXANK (regulatory factor X-associated ankyrin-containing protein), SMAD3 (SMAD family member 3), TNFRSF1B (tumor necrosis factor receptor superfamily, member 1B), VIM (vimentin), CD24 (CD24 molecule), DAP (death-associated protein), HLA-DRB1 (major histocompatibility complex, class II, DR beta 1), HSPB1 (heat shock 27 kDa protein 1), PRKACA (protein kinase, cAMP-dependent, catalytic, alpha), HDAC5 (histone deacetylase 5), CDC25B (cell division cycle 25 homolog B), TGIF (TGFB-induced factor homeobox 1) and TGFBI (transforming growth factor, beta-induced, 68 kDa);

wherein said reference gene expression profile comprises a reference expression value for said one or more gene(s), said reference expression profile being derived from a comparison of:

(i) a GVHD+ expression profile comprising a GVHD+ expression value for one or more gene(s) derived from a biological sample obtained from a transplant donor known to have induced GVHD in a transplant recipient with (ii) a GVHD– expression profile comprising a GVHD– expression value for one or more gene(s) derived from a biological sample obtained from a transplant donor known to have not induced GVHD in a transplant recipient, whereby said reference expression value is determined as being the level of expression midway between said GVHD+ and GVHD– expression values whereby said midway level separates a GVHD+ class comprising said GVHD+ expression value from a GVHD− class comprising said GVHD− expression value; the level of expression between said GVHD+ and GVHD− expression values defined as separating expression values into GVHD+ and GVHD− classes on the basis of discriminatory analysis; or both; and
  (b) assessing risk of said candidate transplant donor of inducing graft versus host disease (GVHD) in a transplant recipient in accordance with said comparison of said candidate gene expression profile with said reference gene expression profile.

In an embodiment, a candidate expression value within said GVHD+ class is indicative that said candidate transplant donor has an increased risk of inducing GVHD in a transplant recipient.

In another embodiment, a candidate expression value within said GVHD− class is indicative that said candidate transplant donor has a reduced/decreased risk of inducing GVHD in a transplant recipient.

In another aspect, the present invention relates to a method (e.g., an in vitro method) of assessing risk, of a candidate transplant donor, of inducing graft versus host disease (GVHD) in a transplant recipient, said method comprising:
  (a) comparing a gene expression profile derived from a biological sample from said candidate transplant donor to a corresponding reference gene expression profile, wherein the gene expression profile comprises an expression value for one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI; and
  (b) assessing risk of said candidate transplant donor of inducing graft versus host disease (GVHD) in a transplant recipient in accordance with said comparison.

In an embodiment, the above-mentioned reference gene expression profile is obtained from a transplant donor known to have induced GVHD in a transplant recipient, and a differential expression profile is indicative that the candidate transplant donor has a reduced risk of inducing GVHD in a transplant recipient.

In another embodiment, the above-mentioned reference gene expression profile is obtained from a transplant donor known to have induced GVHD in a transplant recipient, and a substantially similar expression profile is indicative that the candidate transplant donor has an increased risk of inducing GVHD in a transplant recipient.

In another embodiment, the above-mentioned reference gene expression profile is obtained from a transplant donor known to have not induced GVHD in a transplant recipient, and a differential expression profile is indicative that the candidate transplant donor has an increased risk of inducing GVHD in a transplant recipient.

In another embodiment, the above-mentioned reference gene expression profile is obtained from a transplant donor known to have not induced GVHD in a transplant recipient, and a substantially similar profile is indicative that the candidate transplant donor has a reduced risk of inducing GVHD in a transplant recipient.

The term "gene expression profile" or "expression profile" of a biological sample refers to a set of values representing nucleic acid (e.g. mRNA) or polypeptide levels of one or more genes in the sample. An expression profile may comprise, for example, values representing expression levels of at least about 2 genes, at least about 5 genes, at least about 10 genes, or at least about 50, 100, 200 or more genes. A biological sample within the scope of the present invention may be any biological sample that includes cellular material from which DNA, RNA or polypeptide (protein) may be isolated. The expression level of a gene may be determined by the amount of DNA, RNA or protein present in the sample which corresponds with the gene. The gene expression profile therefore, may include levels of DNA, RNA and/or protein correlated to specific genes within the biological sample.

A "candidate" gene expression profile is determined in a biological sample from a candidate donor. In the methods of the invention, the candidate gene profile may be compared to a corresponding "reference" gene expression profile in order to assess risk of inducing GVHD in a recipient.

Such a reference gene profile is determined by comparing (i) one or more GVHD+ reference profiles determined in biological samples obtained from donors known to have induced GVHD in a recipient with (ii) one or more GVHD− reference profiles determined in biological samples obtained from donors known to have not induced GVHD in a recipient. The reference profile comprises reference expression values for the one or more genes noted herein. A "reference expression value" (or "separating reference value" or "discriminating reference value") for a given gene lies between the GVHD+ and GVHD− reference values for that gene and divides all expression values into two classes: (1) those lying on the side or zone of the reference value comprising the GVHD+ reference value and (2) those lying on the side or zone of the reference value comprising the GVHD− reference value. As such, GVHD+ and GVHD− classes of expression values are defined for each of said one or more genes, and whether a candidate expression value for a given gene falls within the GVHD+ or GVHD− class allows an assessment of risk accordingly. Such a reference expression value, which defines a boundary separating two classes, may also be referred to as a "separatrix".

In an embodiment, the reference value is determined by discriminatory analysis (e.g., Linear Discriminant Analysis (LDA), Quadratic Discriminant Analysis (QDA)), on the basis of the GVHD+ and GVHD− reference values available.

In an embodiment, the reference value is the level of expression midway between the GVHD+ and GVHD− reference values. In such a case, a candidate expression value which lies closer to the GVHD+ reference value than the GVHD− reference value would fall within the GVHD+ class. Similarly, in such a case, a candidate expression value which lies closer to the GVHD− reference value than the GVHD+ reference value would fall within the GVHD− class.

The present invention further relates to a method of assessing risk, of a candidate transplant donor, of inducing graft versus host disease (GVHD) in a transplant recipient, said method comprising determining, in a biological sample from said candidate donor, the level of expression, at the nucleic acid or polypeptide level, of one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI, wherein an alteration in said level of expression relative to a corresponding reference level of expression is indicative that said candidate donor has a reduced risk of inducing GVHD in a transplant recipient.

In an embodiment, the level of expression of the above-mentioned gene(s) is determined by determining the level of expression of one or more nucleic acid(s) or polypeptide(s) encoded thereby comprising a sequence selected from SEQ ID NOs: 1-206 (odd numbers represent nucleic acid sequences, even numbers represent polypeptide sequences).

Expression levels may in general be detected by either detecting mRNA from the cells and/or detecting expression products, such as polypeptides and proteins. Expression of the transcripts and/or proteins encoded by the nucleic acids described herein may be measured by any of a variety of known methods in the art. In general, the nucleic acid sequence of a nucleic acid molecule (e.g., DNA or RNA) in a patient sample can be detected by any suitable method or technique of measuring or detecting gene sequence or expression. Such methods include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level.

Expression levels may be represented by any form of data which is suitable for use in the methods (e.g., comparisons and assessments) described herein. In embodiments, such data may be recorded on a computer-readable medium.

Methods to measure protein expression levels of selected genes of this invention are well known in the art. Examples of such methods include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the protein including but not limited to DNA binding, ligand binding, or interaction with other protein partners.

Methods for normalizing the level of expression of a gene are well known in the art. For example, the expression level of a gene of the present invention can be normalized on the basis of the relative ratio of the mRNA level of this gene to the mRNA level of a housekeeping gene or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the ACTIN gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene® QPCR Human Reference Total RNA, Clontech™ Universal Reference Total RNA, and XpressRef™ Universal Reference Total RNA.

Further, the normalization and calibration of gene expression may be performed in a straightforward manner for predictive models that involve pairs of predictive genes in competitive relationships, i.e. ratio of gene 1 over gene 2 in a predictive gene pair, obviating the need for additional reference genes (see section on PIA models in Examples). Instead of reporting the level of a predictive gene with respect to a separate housekeeping gene and/or reference sample, the level of predictive gene 1 with respect to predictive gene 2 directly provides for a relative expression measurement ratio with high information content.

Nucleic acid arrays are particularly useful for detecting the expression of the genes of the present invention. The production and application of high-density arrays in gene expression monitoring have been disclosed previously in, for example, PCT Publication No. WO 97/10365; PCT Publication No. WO 92/10588; U.S. Pat. No. 6,040,138; U.S. Pat. No. 5,445,934; or PCT Publication No. WO 95/35505, all of which are incorporated herein by reference in their entireties. Also for examples of arrays, see Hacia et al., Nature Genetics 14:441; Lockhart et al., Nat. Biotechnol. 14:1675-1680; and De Risi et al., Nature Genetics 14:457, each of which is incorporated by reference in its entirety. In general, in an array, an oligonucleotide, a cDNA, or genomic DNA, that is a portion of a known gene, occupies a known location on a substrate. A nucleic acid target sample is hybridized with an array of such oligonucleotides and then the amount of target nucleic acids hybridized to each probe in the array is quantified. One preferred quantifying method is to use confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used. In a particularly preferred embodiment, one can use the knowledge of the genes described herein to design novel arrays of polynucleotides, cDNAs or genomic DNAs for screening methods described herein. Such novel pluralities of polynucleotides are contemplated to be a part of the present invention and are described in detail below.

Suitable nucleic acid samples for screening on an array contain transcripts of interest or nucleic acids derived from the transcripts of interest (i.e., transcripts derived from the genes associated with reduced risk of inducing GVHD in a transplant recipient of the present invention). As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like. Preferably, such a sample is a total RNA preparation of a biological sample (e.g., peripheral blood mononuclear cells or PBMCs, immune cells, immune cell subpopulations). More preferably in some embodiments, such a nucleic acid sample is the total mRNA isolated from such a biological sample.

Methods of isolating total mRNA are well known to those of skill in the art. In one embodiment, the total nucleic acid is isolated from a given sample using, for example, an acid guanidinium-phenol-chloroform extraction method and polyA and mRNA is isolated by oligo dT column chromatography or by using (dT)n magnetic beads (see, e.g., Sambrook et al., Molecular Cloning: A Laboratory Manual (2nd ed.), Vols. 1-3, Cold Spring Harbor Laboratory, (1989), or Current Protocols in Molecular Biology, F. Ausubel et al., ad. Greene Publishing and Wiley-Interscience, New York (1987)).

In an embodiment, the above-mentioned reference gene expression profile is contained within a database. As used herein the term "database" or "gene expression database" refers to the expression profiles for a given sample type or types. A plurality of gene expression profiles may be used to generate the gene expression database. The gene expression profiles are statistically analysed to identify gene expression levels that characterise particular sample types (e.g., a sample associated with "high risk" or "low risk" of inducing GVHD in a transplant recipient).

In another embodiment, the above-mentioned comparing is carried out using a computer algorithm. Examples of well-known algorithms includes linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; recursive feature elimination or entropy-based recursive feature elimination algorithms; a plurality of algorithms arranged in a committee network; and forward floating search or backward floating search algorithms.

The gene expression profiles useful for the method of the invention (e.g. a reference expression profile) can be provided on an electronic media that can be automatically read such as computer readable media (magnetic, optical, and the like). This media can be part of a kit that can also include instructions for assessing the gene expression profiles in such media. For example, the kit may comprise a CD-ROM having computer instructions for comparing gene expression profiles of the portfolios of genes described above. The kit may also have gene expression profiles (e.g. a reference gene expression profile) digitally recorded therein so that they may be compared with gene expression data from subject samples (e.g., candidate transplant donors). The kit may also comprise a data analysis tool (e.g., a computer program) that permits the comparison of gene expression profiles.

In another aspect, the present invention provides a GVHD risk assessment expression profile map comprising gene expression level information for one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI.

In an embodiment, the above-mentioned expression profile map is digital information stored in a computer-readable medium. The term "computer readable medium" refers to any device or system for storing or providing information (e.g., data and instructions) to a computer processor. Examples of computer readable media include, but are not limited to, DVDs, CDs, hard disk drives, magnetic tape and servers for streaming media over networks.

The term "GVHD risk assessment expression profile map" refers to a presentation of expression levels of a set of genes in a biological sample from a particular type of transplant donor (e.g., a transplant donor known to have induced GVHD in a recipient, or a transplant donor known to have not induced GVHD in a recipient). The map may be presented as a graphical representation (e.g., on paper or a computer screen), a physical representation (e.g., a gel or array) or a digital representation stored in a computer-readable medium. Each map corresponds to a particular type of transplant donor, and thus provides a template for comparison to a candidate transplant donor sample. In embodiments, maps are generated from pooled samples comprising biological samples from a plurality of transplant donors of the same type.

Querying a database of expression profiles with known prognosis (e.g., increased or reduced risk of inducing GVHD in a transplant recipient) can be done in a direct or indirect manner. The "direct" manner is where the subject's (e.g., candidate transplant donor) expression profile is directly compared to other individual gene expression profiles in the database to determine which profile (and hence which prognosis) delivers the best match. Alternatively, the querying may be done more "indirectly", for example, the subject's expression profile could be compared against simply the "standard" profile in the database for a particular prognostic assignment (e.g., "bad", or a prognostic value or range of values). The "standard" profiles may be stored on a relatively inexpensive data carrier or other memory device (e.g. computer system), which may then form part of a kit in accordance with the present invention. By comparing the subject's expression profile to the standard profile and the pre-determined statistical variation in the population, it is also be possible to deliver a "confidence value" as to how closely the subject's expression profile matches the "standard" profile.

In an embodiment, the above-mentioned one or more gene(s) is selected from the group consisting of FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI, and said one or more gene(s) shows (a) higher expression in biological samples from transplant donors having a reduced/decreased risk of inducing GVHD in a recipient and/or (b) lower expression in biological samples from transplant donors having an increased/elevated risk of inducing GVHD in a recipient.

In another embodiment, the above-mentioned one or more gene(s) is selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD and PPIE, and said one or more gene(s) shows higher expression in biological samples from transplant donors having an increased or elevated risk of inducing GVHD in a recipient and/or lower expression in biological samples from transplant donors having a reduced/decreased risk of inducing GVHD in a recipient.

In an embodiment, the above-mentioned biological sample comprises a CD4$^+$ T cell and the above-mentioned one or more gene(s) is selected from RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, RFXANK, SMAD3, VIM, CDC25B, TGIF and TGFBI. In a further embodiment, the above-mentioned one or more gene(s) is selected from TCIRG1, SMAD3, ATBF1, AKT2, CD151, SIL, FNBP3, EP300, NMI, FURIN, TGIF and TGFBI.

In another embodiment, the above-mentioned biological sample comprises a CD8$^+$ T cell and the above-mentioned one or more gene(s) is selected from CD3D, CD1A, IL15RA, IL2RG, ILF1, LAT, MGMT, TLR1, RGS13, THBS1, TCIRG1, PIAS4, NFAT5, BAG3, VEGF, YY1, FURIN, CCND1, CHERP, CSDA, DOK2, FOXJ1, MCAM, NFKB2, PTGER4, DAD1, ILF3, RFXANK, SMAD3, TNFRSF1B, VIM, CD24, DAP, HLA-DRB1, HSPB1, PRKACA, HDAC5 and CDC25B. In a further embodiment, the above-mentioned one or more gene(s) is selected from CD24, NFAT5 and TCIRG1.

In another embodiment, the above-mentioned biological sample comprises a CD4$^+$ T cell and the above-mentioned one or more gene(s) is selected from CXCR6, SMAD1, FAF1, BCAP31, RANBP2, SNRPN, SOCS5, ANXA5, CD63, CD81, CKS2, CPE, MAD, MYCL1, PDCD8, RHOA, SKP2 and YWHAQ.

In another embodiment, the above-mentioned biological sample comprises a CD8$^+$ T cell and the above-mentioned one or more gene(s) is selected from FAF1, SH3KBP1, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, SOCS5, ANXA5, CD81, CKS2, MYCL1, SKP2, YWHAQ, GAPD, PPIE and RAN. In a further embodiment, the above-mentioned one or more gene(s) is PRF1 and/or SH3KBP1.

In another embodiment, the above-mentioned one or more gene(s) is associated with Transforming Growth Factor beta (TGF-β) or TGF-β signalling/pathway. In a further embodiment, the above-mentioned one or more gene(s) is selected from SMAD3, TGIF, PRF1, FNBP3, TGFBI, EP300 and FURIN.

In general, typical biological samples include, but are not limited to, sputum, serum, lymphatic fluid, blood, blood cells (e.g., peripheral blood mononuclear cells), tissue or fine needle biopsy samples, urine, peritoneal fluid, colostrums, breast milk, fetal fluid, tears, and pleural fluid, or cells therefrom. In embodiments, the determination of expression levels is performed using peripheral blood mononuclear cells (PBMCs), such as immune cells, such as T cells, such as CD4$^+$ and CD8$^+$ T cells.

In an embodiment, the above-mentioned GVHD is acute GVHD (aGVHD). In another embodiment, the above-mentioned GVHD is chronic GVHD (cGVHD).

In further embodiments, the invention relates to the use of nucleic acid(s) (e.g., a probe(s)) which is substantially identical or substantially complementary (e.g., for hybridization under suitable conditions) to a nucleic acid sequence selected from the group consisting of nucleic acid sequences among SEQ ID NOs: 1-206 (odd numbers represent nucleic acid sequences), a complement thereof, or a portion thereof.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid or polypeptide sequence is "homologous" to another sequence if the two sequences are substantially identical and the functional activity of the sequences is conserved (as used herein, the term 'homologous' does not infer evolutionary relatedness). Two nucleic acid or polypeptide sequences are considered "substantially identical" if, when optimally aligned (with gaps permitted), they share at least about 50% sequence similarity or identity and/or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs: 1-206. "Substantially complementary" nucleic acids are nucleic acids in which the complement of one molecule is substantially identical to the other molecule.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BEST-FIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In an embodiment, it is desirable to amplify the nucleic acid sample prior to hybridization. One of skill in the art will appreciate that whatever amplification method is used, if a quantitative result is desired, a method is used that maintains or controls for the relative frequencies of the amplified nucleic acids to achieve quantitative amplification. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. For example, a high-density array may then include probes specific to the internal standard for quantification of the amplified nucleic acid. Other suitable amplification methods include, but are not limited to polymerase chain reaction (PCR) Innis, et al., PCR Protocols. A guide to Methods and Application. Academic Press, Inc. San Diego, (1990)), ligase chain reaction (LCR) (see Wu and Wallace, Genomics, 4: 560, Landegren, et al., Science, 241: 1077 and Barringer, et al., Gene, 89: 117), transcription amplification (Kwoh, et al., Proc. Natl. Acad. Sci. USA, 86: 1173), and self-sustained sequence replication (Guatelli, et al, Proc. Nat. Acad. Sci. USA, 87: 1874).

Another aspect of the present invention relates to one or more polynucleotide oligonucleotides (probes and/or primers) for the detection of the expression of genes that are selectively regulated in a biological sample from a transplant donor with increased or reduced risk of inducing GVHD in a recipient, to determine a gene expression profile.

In another aspect, the present invention provides a collection of two or more isolated nucleic acids encoding one or more gene(s) selected from the group consisting of CXCR6, SMAD1, FAF1, SH3KBP1, HDAC2, IL1R1, CDC42, GADD45G, IFNAR2, IFRD1, IGFBP2, IRF3, LIG4, MAP2K1, MME, RASGRP1, STAT1, TFRC, TRIM22, TFAP2C, CDC25A, GSR, PRF1, BCAP31, RANBP2, SNRPN, SOCS5, ANXA5, CD63, CD81, CKS2, CPE, MAD, MYCL1, PDCD8, RHOA, SKP2, YWHAQ, GAPD, PPIE, RAN, FOSB, MAP2K6, SERPINB2, TLR4, CD3D, GAB2, MAPK8IP1, SMO, CD151, EP300, FNBP3, IL6R, NMI, PDK2, PPP1R16B, SIL, SNRP70, STK38, TCIRG1, CD1A, IL15RA, IL2RG, ILF1, LAT, MGMT, TLR1, RGS13, THBS1, NFAT5, PIAS4, ADD1, BAG3, VEGF, YY1, AKT2, FURIN, ATBF1, CCND1, CHERP, CSDA, DOK2, FOXJ1, HEXA, LAMP2, MCAM, NFKB2, PTGER4, DAD1, ILF3, RFXANK, SMAD3, TNFRSF1B, VIM, CD24, DAP, HLA-DRB1, HSPB1, PRKACA, HDAC5, CDC25B, TGIF and TGFBI, their complements, or portions or fragments thereof.

In an embodiment, the above-mentioned nucleic acids comprise a sequence selected from the group consisting of SEQ ID NOs: 1-206 (odd numbers represent nucleic acid sequences).

An "oligonucleotide" is meant to include a nucleic acid oligomer that hybridizes specifically to a target sequence in a nucleic acid or its complement, under conditions that promote hybridization, thereby allowing detection of the target sequence or its amplified nucleic acid. Detection may either be direct (i.e, resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e., a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled.

The polynucleotide probe(s) of the invention consist(s) of, or consist(s) essentially of, one or more polynucleotide probes that are complementary to RNA transcripts, or nucleotides derived therefrom, of at least one nucleic acid sequence that has been identified herein, or its complement. The plurality of polynucleotides within the above-limitation includes at least one or more polynucleotide probes (e.g., at least 1, 2, 3, 4, 5, 6, and so on, in whole integer increments, up to the maximum number of possible probes) that are complementary to RNA transcripts, or nucleotides derived therefrom, of at least one gene, and preferably, at least 2 or more genes described herein. Such genes are selected from any of the genes listed in the tables provided herein and can include any number of genes, in whole integers (e.g., 1, 2, 3, 4, . . . ). Multiple probes can also be used to detect the same gene or to detect different splice variants of the same gene. In an aspect, each of the polynucleotides is at least 5 nucleotides in length. In an aspect, the polynucleotide probe(s) consist(s) of at least one polynucleotide probes, wherein each polynucleotide probe is at least 5 nucleotides in length, and wherein each polynucleotide probe is complementary to an RNA transcript, or nucleotide derived therefrom, of a gene comprising, or expressing a transcript comprising, a nucleic acid sequence selected from the group consisting of SEQ ID NOs: 1-206 (odd numbers represent nucleic acid sequences). In another aspect, the polynucleotide probe(s) comprise(s) polynucleotides that are complementary to an RNA transcript, or a nucleotide derived therefrom, of at least two genes comprising, or expressing a transcript comprising, a nucleic acid sequence selected from the group consisting of nucleic acid sequences among SEQ ID NOs: 1-206 (odd numbers represent nucleic acid sequences). In another aspect, the polynucleotide probe(s) comprises polynucleotide probes that are complementary to an RNA transcript, or a nucleotide derived therefrom, of at least five genes, at least 10 genes, at least 25 genes, at least 50 genes, or up to all of the genes, comprising, or expressing a transcript comprising, a nucleic acid sequence selected from the group consisting of SEQ ID NOs: 1-206 (odd numbers represent nucleic acid sequences).

In accordance with the present invention, an isolated polynucleotide, or an isolated nucleic acid molecule, is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. The polynucleotides useful in the polynucleotide probes of the present invention are typically a portion/fragment of a gene (sense or non-sense strand) of the present invention that is suitable for use as a hybridization probe or PCR primer for the identification of a full-length gene (or portion/fragment thereof) in a given sample (e.g., a peripheral blood cell sample). An isolated nucleic acid molecule can include a gene or a portion of a gene (e.g., the regulatory region or promoter), for example, to produce a reporter construct according to the present invention. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

The minimum size of a nucleic acid molecule or polynucleotide of the present invention is a size sufficient to form a probe or oligonucleotide primer that is capable of forming a stable hybrid with the complementary sequence of a nucleic acid molecule encoding the natural protein (e.g., under moderate, high or very high stringency conditions), or to otherwise be used as a target in an assay or in any therapeutic method discussed herein. If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater (1000, 2000, etc.), including any length in between, in whole number increments (i.e., 5, 6, 7, 8, 9, 10, . . . 33, 34, . . . 256, 257, . . . 500 . . . 1000 . . . ), and more preferably from about 10 to about 40 nucleotides, and most preferably from about 15 to about 40 nucleotides in length. There is no limit, other than a practical limit, on the maximal size of a nucleic acid molecule of the present invention, in that the nucleic acid molecule can include a portion of a protein-encoding sequence or a nucleic acid sequence encoding a full-length protein.

In an embodiment, the polynucleotide probes are conjugated to detectable markers. Detectable labels suitable for use in the present invention include any composition detectable by spectroscopic, photochemical, biochemical, immunochemical, electrical, optical or chemical means. Useful labels in the present invention include biotin for staining with labeled streptavidin or avidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Preferably, the polynucleotide probes are immobilized on a substrate.

In one embodiment, the polynucleotide probes are hybridizable array elements in a microarray or high density array. The term "microarray" refers to an ordered arrangement of hybridizable array elements, preferably polynucleotide/nucleic acid probes, on a substrate. Nucleic acid arrays are well known in the art and are described for use in comparing expression levels of particular genes of interest, for example, in U.S. Pat. No. 6,177,248, which is incorporated herein by reference in its entirety. Nucleic acid arrays are suitable for quantifying small variations in expression levels of a gene in the presence of a large population of heterogeneous nucleic acids. Knowing the identity of the genes set forth by the present invention, nucleic acid arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. It is noted that all of the genes described herein have been previously sequenced, at least in part, such that oligonucleotides suitable for the identification of such nucleic acids can be produced. The database accession number for each of the genes described herein is provided in the tables herein. Suitable nucleic acids are also produced by amplification of template, such as by polymerase chain reaction or in vitro transcription.

One of skill in the art will appreciate that an enormous number of array designs are suitable for the practice of the invention. An array will typically include a number of probes that specifically hybridize to the sequences of interest. In addition, an array may also include one or more control probes and/or "test probes." Test probes could be for example oligonucleotides having a minimum or maximum length as described above for other oligonucleotides. Test probes may be double or single strand DNA sequences. DNA sequences are isolated or cloned from natural sources or amplified from natural sources using natural nucleic acids as templates, or produced synthetically. These probes have sequences complementary to particular subsequences of the genes whose expression they are designed to detect. Thus, the test probes are capable of specifically hybridizing to the target nucleic acid they are to detect.

In an example of the microarray technique, PCR amplified inserts of cDNA clones are applied to a substrate in a dense array. The microarrayed genes, immobilized on the microchip, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labelled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106-149 (1996)). Microarray analysis can be performed by commercially available equipment, following manufacturers protocols, such as by using the Affymetrix GenChip technology, or Incyte's microarray technology.

Another embodiment of the present invention relates to a reagent which specifically binds with the polypeptide, such as chemical agents, or natural products, or antibodies, or antigen binding fragments thereof, e.g., for the detection of the expression of genes regulated in biological samples from a transplant donor with reduced or increased risk of inducing GVHD in a recipient. In embodiments, the reagent comprises chemical agents, or natural products, or antibodies, or antigen binding fragments thereof, that selectively bind to proteins encoded by genes that are regulated in biological samples from transplant donors, and that can be detected as protein products using antibodies. In addition, the reagent comprises chemical agents, or natural products, or antibodies, or antigen binding fragments thereof, that selectively bind to proteins or portions thereof (peptides) encoded by one or more genes selected from SEQ ID NOs: 1-206 (even numbers represent polypeptide sequences). In an aspect, the reagent consists of one or more antibodies, antigen binding fragments thereof, or antigen binding peptides, each of which selectively binds to a protein encoded by a gene comprising, or expressing a transcript comprising, a nucleic acid sequence selected from the group consisting of SEQ ID NOs: 1-206.

According to the present invention, the phrase "selectively binds to" refers to the ability of a chemical agent, a natural product, an antibody, antigen-binding fragment or binding partner (antigen binding peptide) to preferentially bind to specified proteins. More specifically, the phrase "selectively binds" refers to the specific binding of one protein to another molecule (e.g., chemical agent, natural product, an antibody, fragment thereof, or binding partner to an antigen), wherein the level of binding, as measured by any standard assay (e.g., an immunoassay, fluorescence), is statistically significantly higher than the background control for the assay. For example, when performing an immunoassay, controls typically include a reaction well/tube that contain chemical agent, natural product, antibody or antigen binding fragment alone (i.e., in the absence of antigen), wherein an amount of reactivity (e.g., non-specific binding to the well) by the chemical agent, natural product, antibody or antigen binding fragment thereof in the absence of the antigen is considered to be background. Binding can be measured using a variety of methods standard in the art including enzyme immunoassays (e.g., fluorescence, ELISA, immunoblot assays, etc.).

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Generally, in the production of an antibody, a suitable experimental animal, for example, an animal including but not limited to a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

For diagnostic or risk assessment applications, the reagent (i.e., the antibodies or antigen binding fragments thereof) is either in a free state or immobilized on a solid support, such as a tube, a bead, a microarray or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. Indirect means may also employ a ligand-receptor system, for example, where a molecule such as a vitamin is grafted onto the reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horseradish peroxidase or luciferase or alkaline phosphatase, or a radioactive element such as $^{125}I$ or $^{51}Cr$.

The invention also features kits for assessing a patient's risk for complications following transplantation (e.g., for developing GVHD). The kits can include reagents for evaluating the expression or activity of genes (nucleic acids (e.g., mRNAs) or proteins) that play a role in the processes that support successful engraftment or that discourage engraftment. Kits for evaluating expression of nucleic acids can include, for example, probes or primers that specifically bind a nucleic acid of interest (e.g., a nucleic acid, the expression of which correlates with increased risk of complications following transplantation). The kits for evaluating nucleic acid expression can provide substances useful as standard (e.g., a sample containing a known quantity of a nucleic acid to which test results can be compared, with which one can assess factors that may alter the readout of a diagnostic test, such as variations in an enzyme activity or binding conditions). Kits for assessing nucleic acid expression can further include other reagents useful in assessing levels of expression of a nucleic acid (e.g., buffers and other reagents for performing PCR reactions, or for detecting binding of a probe to a nucleic acid). In addition to, or as an alternative, kits can include reagents for detecting proteins (e.g., antibodies). The kits can provide instructions for performing the assay used to evaluate gene expression instructions for determining risk based on the results of the assay. For example, the instructions can indicate that levels of expression of a gene of interest (e.g., relative to a standard or a control), correlate with increased risk for an adverse outcome from transplantation. Kits can also provide instructions, containers, computer readable media (comprising, for example, a data analysis program, a reference gene expression profile, etc.), control samples, and other reagents for obtaining and processing samples for analysis.

The invention further provides methods for developing personalized treatment plans. Information gained by way of the methods described above can be used to develop a personalized treatment plan for a transplant recipient. Accordingly, the invention further provides methods for developing personalized treatment plans for transplant recipients. The methods can be carried out by, for example, using any of the methods of gene analysis described above and, in consideration of the results obtained, designing a treatment plan for the transplant recipient. If the levels of gene expression indicate that the recipient is at risk for an undesirable clinical outcome (e.g., development of a GVHD), the recipient is a candidate for treatment with an effective amount of an anti-rejection agent. Depending on the level of gene expression or the gene expression profile, the recipient may require a treatment regime that is more or less aggressive than a standard regime, or it may be determined that the recipient is best suited for a standard regime. When so treated, one can treat or prevent complications associated with transplantation such as GVHD. Conversely, a different result (i.e., a different level of expression of certain genes) may indicate that the patient is not likely to experience an undesirable clinical outcome. In that event, the patient may avoid anti-rejection agents (or require a less aggressive regime) and their associated side effects.

The anti-rejection therapy, if deemed advisable, can be carried out with any of the presently used therapeutic agents. Generally, these agents are suspended in carriers/excipients (physiological saline) and administered orally or by inhalation or intravenous infusion, or injected or implanted in a variety of ways (e. or intramuscularly). The standard dosage may be increased or decreased, depending on the results of the gene expression analysis. For example, dosage may be at least 2-fold, 3-fold, 4-fold, 6-fold, 8-fold, 10-fold, 20-fold, 50-fold, 100-fold, or 150-fold more or less than the dosage the patient would ordinarily receive.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Materials and Methods

Patients.

Only patients with hematological malignancies, and their healthy HLA-genotypically identical sibling donors, participated in this study. The AHCT myeloablative regimen consisted of cyclophosphamide (120 mg/kg) and total body irradiation (12 Gy), or busulfan (16 mg/kg) and cyclophosphamide (200 mg/kg). All patients received unmanipulated peripheral blood stem cell grafts (mobilized with G-CSF) and were given GVHD prophylaxis consisting of cyclosporine A and short course methotrexate (von Bueltzingsloewen et al., Blood 81:849). Donor blood samples were obtained one day prior to mobilization of peripheral blood progenitor cells with G-CSF. Diagnosis of aGVHD and cGVHD was made after clinical evaluation and histologic confirmation according to previously reported criteria (Vogelsang et al., (2003). Annu. Rev. Med 54:29; Poulin et al., (2003). Blood 102:4600; Przepiorka et al., (1995). Bone Marrow Transplant. 15:825). Patients with grade 0 and grade I-IV aGVHD were considered aGVHD- and aGVHD+, respectively (Przepiorka et al., supra). All subjects with cGVHD showed clinical extensive GVHD (Vogelsang et al., supra).
RNA Isolation, Amplification and Microarray Hybridization.

Sample RNA was extracted using an RNA extraction kit (Qiagen), then amplified using the MessageAmp™ RNA kit (Ambion) as per the manufacturer's instructions. Universal human RNA (Stratagene) was prepared in the same way. Sample probes were prepared by direct labeling with 3 μg of the aRNA Cy-5 (R values) fluorescent dye while the universal RNA probes were prepared by direct labeling of universal aRNA with Cy-3 (G values). All patient samples were hybridized against amplified universal aRNA at 37° C. for 18 h on microarrays. Detailed information on the microarrays as well as the labeling and hybridization procedures are described in Jansova et al., (2006). Clin. Genet. 69: 218 and Bosinger et al., (2004). J Immunol. 173(11):6858).

Microarray Data Pre-Processing

Microarrays were scanned at 16 bits using the ScanArray Express Scanner™ (Packard Bioscience) at 10-μm resolution at 635 (R) and 532 (G) nm wavelengths for cy-5 and cy-3 respectively to produce image (tiff) files that were quantified using Genepix Pro™ 6.0 image analysis software (Molecular Devices Corporation). Bad spots were flagged manually according to their morphologies. The results were saved as Quantarray™ files (QAF), where the intensity values ranged from 0 to $2^{16}-1$ (65535) units. The tiff and QAF files were compressed and archived for permanent storage and further analysis. The microarrays were then screened for quality, first by visual inspection of the array with flagging of poor quality spots, and second with automated scripts that scanned the quantified output files and measured overall density distribution on each channel and number of flagged spots. Box-plots, MA-plots, and density distribution plots were drawn and inspected. Each quantified output file was run though the following pre-processing steps using the R language and environment Wit et al., 2004. Statistics for Microarrays: Design, Analysis and Inference. John Wiley and Sons Ltd, England. 1-265 pp.; Dalgaard, 2002. *Introductory Statistics with R*. Springer. 1-288 pp.; Maindonald et al., 2003. *Data Analysis and Graphics Using R*. Cambridge University Press, Cambridge. 1-362 pp.; Everitt et al., 2006. *A Handbook of Statistical Analyses using R*. Chapman & Hall/CRC, Boca Raton, Fla. 1-304 pp.) and the Limma package (Smyth, (2005). Bioinformatics and Computational Biology Solutions using R and Bioconductor, 397-420). For minimum intensity filtering, R and G values were treated with a surrogate replacement policy for estimating sub-threshold values. For normalization within arrays, the raw merged R and G channels were lowess-normalized (grouped by print-tip) and transformed to log 2 ratios (Smyth, supra; and Fukunaga, Introduction to Statistical Pattern Recognition (Second Edition), Academic Press, New York, 1990, 1-592 pp.). The commensurability of average brightness between the arrays of a pool of arrays was then assured using zero-centering of log-distributions normalization. When both duplicate spots of a clone (gene) passed quality control, the average profile of the replicate clones was calculated and used as the representative profile for that gene. If only one of the clone duplicate spots passed quality control, only that profile was used in the downstream analysis. All data were then represented as log 10 (Red/Green) expression ratios for further analysis.

qRT-PCR

Total RNA were reverse transcribed in a final volume of 50 μL using the High Capacity cDNA Archive Kit™ with random primers (Applied Biosystems) as described by the manufacturer. Reverse transcribed samples were quantified using spectrophotometer measurements, diluted to a concentration of 5 ng/μl, and stored at -20° C. A reference RNA (Human reference total RNA, Stratagene, Ca) was also transcribed to cDNA and was used as the calibrator. Gene expression level was determined using the following primer and probe sets obtained commercially from Applied Biosystems (ABI Assays on Demand™ http://www.appliedbiosystems.com/): AKT2 (Hs00609846_m1), ATBF1 (Hs00199344_m1), CD151 (Hs00170407_m1), EP300 (Hs00230938_m1), FAF1 (Hs00169544_m1), FURIN (Hs00159829_m1), IL1R1 (Hs00991001_m1), IL6R (HS00794121_m1), MYCL1 (Hs00607136_g1), NMI (Hs00190768_m1), PDCD8 (Hs00377585_m1), RAN (Hs00741099_g1), SH3KBP1 (Hs00230414_m1), SIL (Hs00161700_m1), SMAD3 (Hs00706299_s1), STK38 (Hs00179367_m1), TCIRG1 (Hs00246039_m1), TGFBI (Hs00165908_m1), TGIF (Hs00820148_g1), FNBP3 (Hs00215465_m1), NFAT5 (Hs00232437_m1), PRF1 (Hs00169473_m1), CD24 (Hs02379687_s1). The human GAPDH (glyceraldehyde-3-phosphate dehydrogenase) pre-developed TaqMan™ assay (PN4326317E) was used as endogenous control. PCR reactions were performed using 4 μl of cDNA samples (20 ng), 5 μl of the TaqMan Universal PCR Master Mix™ (Applied Biosystems) and 0.5 μl of the TaqMan™ Gene Expression Assays (20×) in a total volume of 10 μl. The ABI PRISM™ 7900HT Sequence Detection System (Applied Biosystems) was used to detect the amplification level and was programmed to an initial step of 10 minutes at 95° C., followed by 40 cycles of 15 seconds at 95° C. and 1 minute at 60° C. All reactions were run in triplicate and the average values were used for quantification. The relative quantification of target genes was determined by using the ΔΔCT method. Briefly, the Ct (threshold cycle) values of target genes were normalized to an endogenous control gene (GAPDH) ($\Delta CT = Ct_{target} - Ct_{GAPDH}$) and compared with a calibrator (Human reference RNA): $\Delta\Delta CT = \Delta Ct_{sample} - \Delta Ct_{Calibrator}$. Relative expression (RQ) was calculated using the Sequence Detection System (SDS) 2.2.2 software (Applied Biosystems) and the formula $RQ = 2^{-\Delta\Delta CT}$.

Predictive Interaction Analysis (PIA)

PIA was carried out on the 105 gene pairs formed by 15 genes that were individually predictive of GVHD in both microarray and qRT-PCR experiments. Gene pairs and single genes were compared as to their ability to distinguish GVHD+ from GVHD- samples according to the statistical methods outlined below.

1) Two-Class Discriminant Analysis.

Standard equations of LDA (Linear Discriminant Analysis) (Fukunaga, supra) are employed for determining two-class separations (GVHD+ vs. GVHD-), based on single-gene or two-gene abundances. Column vector $\vec{x}$ represents the log 10 abundances of a gene pair. T denotes transpose. c1 denotes one known class (e.g., GVHD+) and c2 denotes a second known class (e.g., GVHD-). The general two-class linear discriminant equation is: (eq. 1) $f(\vec{x}) = (\vec{\mu}_{c2} - \vec{\mu}_{c1})^T \Sigma^{-1} \vec{x} + (\vec{\mu}_{c1}{}^T \Sigma^{-1} \vec{\mu}_{c1} - \vec{\mu}_{c2}{}^T \Sigma^{-1} \vec{\mu}_{c2})/2 + \ln(P_{c2}/P_{c1})$, where gene pair vectors $\vec{\mu}_{c1}$ and $\vec{\mu}_{c2}$ are the respective class means; $\Sigma^{-1}$ is the inverse of the gene pair by gene pair data-derived pooled covariance matrix $\Sigma$, which is the sample number-weighted sum of the data-derived within-class covariance matrices. $P_{c1}$ and $P_{c2}$ are the prior probabilities of the two classes. The $\ln(P_{c2}/P_{c1})$ term in eq. 1 is zero because we set $P_{c2} = P_{c1}$. In the LDA, the proportion of class 2 samples compared to class 1 samples in the data is not germane. What is germane in the LDA are the individual sample data values, the class means, and the within class variations, not the prior probabilities per se. Setting eq. 1 to zero defines the general equation for the separatrix L: (eq. 2) $\vec{a}^T \cdot \vec{x} + c = 0$, where parameter vector $\vec{a}^T = (\vec{\mu}_{c2} - \vec{\mu}_{c1})^T \Sigma^{-1}$ and scalar $c = (\vec{\mu}_{c1}{}^T \Sigma^{-1} \vec{\mu}_{c1} - \vec{\mu}_{c2}{}^T \Sigma^{-1} \vec{\mu}_{c2})/2$ are data-dependent constants. The general L then can be written immediately in slope\intercept form as (eq. 3) $x_2 = -(a_1/a_2)x_1 - c/a_2$, where $[a_1, a_2] = \vec{a}^T$. However, in the PIA to be described below, a specialized, deliberately constrained form of eq. 3 is used. Namely, the separatrix L has slope $-1$ (SPIA) or $+1$ (CPIA) and bisects the chord between the two class means $\vec{\mu}_{c1}$ and $\vec{\mu}_{c2}$.

2) Competitive and Synergistic Predictive Interaction Analysis (CPIA and SPIA).

As described earlier, the product X×Y for gene X and gene Y represents a synergistic phenomenological gene-gene interaction (SPIA), and the abundance ratio X/Y (or Y/X) for gene X and gene Y represents a competitive phenomenological gene-gene interaction (CPIA). We define $x = \log_{10}(X)$, $y = \log_{10}(Y)$, and new coordinates or axes: $u = x + y$ and $v = x - y$. Class separation in (x, y) with respect to u is termed SPIA, and class separation with respect to v is termed CPIA. PIA refers to either SPIA or CPIA. Hence, good class separation in SPIA is demonstrated by good separation in (x, y) by a separatrix $u = x + y = $ constant (equivalent to $y = -x + $ constant, i.e., slope $-1$), and good class separation in CPIA is demonstrated by good separation in (x, y) by a separatrix $v = x - y = $ constant (equivalent to $y = x - $ constant, i.e., slope $+1$). Thus, we apply LDA under models restricted to separatrices whose slopes are constrained deliberately to $-1$ or $+1$.

3) Classification Performance Measures.

Straightforward sampling statistics was used to characterize class separation by p-values as well as by counts of correctly classified samples relative to the total number of samples being classified (accuracies). The class-separation performance of a gene pair (X,Y) in SPIA or CPIA can be assessed readily on single axes x, y, u, and v. When samples in (x, y) are, for example, projected onto the x-axis, classification performance is assessed by the p-value returned by a simple $\sigma_{C1}{}^2 = \sigma_{C2}{}^2$ two-tailed t-test for differences of two means under $H_0$: $\mu_{x,C1} = \mu_{x,C2}$. This is computed analogously and separately for the y, u, and v axes. We seek gene pairs (X,Y) for which along the "single variable" u-axis or v-axis, the classes separate better than on the x-axis only AND better than along the y-axis only.

Example 2

Experimental Model

In the studies described herein for a GVHD predictive signature, we wished to correlate global gene expression profiling of AHCT donor T cells with the occurrence of GVHD in recipients. A secondary objective was to evaluate whether the donor gene expression profile persisted long-term in the recipient. Peripheral blood was obtained from 50 AHCT donors pre-transplant (referred to as day 0) and from 40 recipients on day 365 (FIG. 1). Donors and recipients were HLA-identical siblings. Recipients were regarded as negative for acute GVHD (aGVHD) when they lived at least 100 days without presenting GVHD. Recipients were considered negative for chronic GVHD (cGVHD) when they remained cGVHD-free for 365 days post-AHCT. CD4$^+$ and CD8$^+$ T-cell subsets were purified with microbeads. Total RNA was purified, amplified, reverse transcribed and hybridized on microarrays as described above. RNA from donor and recipient T cells was hybridized on the human H19K array (19,008 ESTs), and donor T-cell RNA was also hybridized on the ImmunArray (3,411 ESTs from immune related genes). The ImmunArray provides additional genes for better coverage of immune responses to complement the H19K array (Jansova et al., supra and Bosinger et al., supra).

Accordingly, the study design included four features to minimize biological noise. First, unlike recipients of solid organ grafts who inevitably present organ failure (e.g., renal insufficiency), AHCT donors are healthy subjects. This is important because serious ailments (and their treatment) may cause alterations in global gene expression that are significantly greater than the background variation in normal gene expression (Whitney et al., (2003). Proc. Natl. Acad. Sci. U.S.A 100:1896). Second, our studies were performed on purified CD4$^+$ and CD8$^+$ T cells. Third, CD4$^+$ and CD8$^+$ T cells are necessary and sufficient for induction of anti-MiHA GVHD (Korngold et al., (1983). Immunol. Rev. 71:5—Perreault et al., Immunol. Today 19:69), the clinical endpoint of this study. Fourth, AHCT recipients were treated in a single center using standardized therapeutic regimens and uniform criteria for diagnosis of GVHD.

Example 3

Donor T-Cell Gene Expression Profiling Using Microarrays

Figures 2A, 2B, 2C:
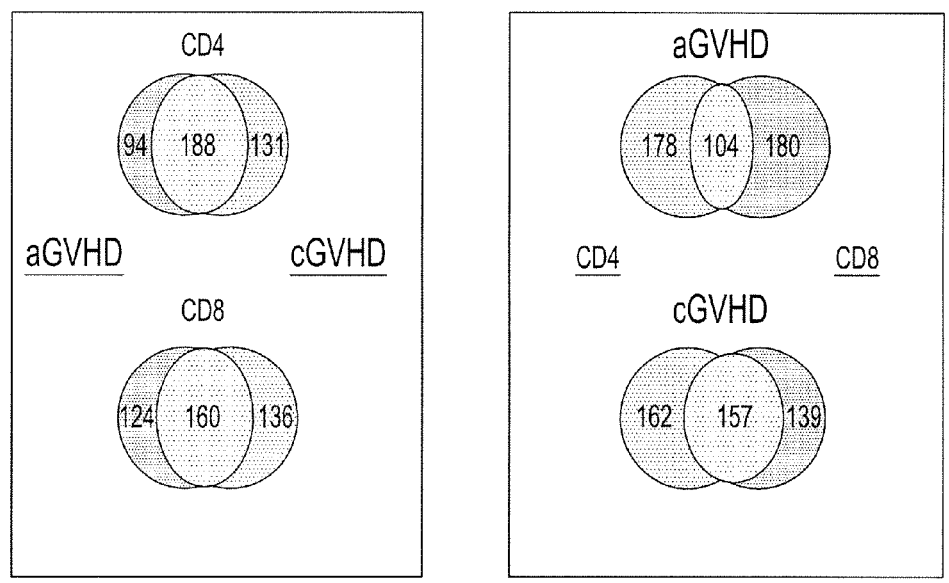
FIGS. 2A-2C: GVHD predictive genes identified by one-dimensional analyses. Searches were performed using two methods: a statistical F-test and linear discriminant analysis-based system.
Figure 4A:
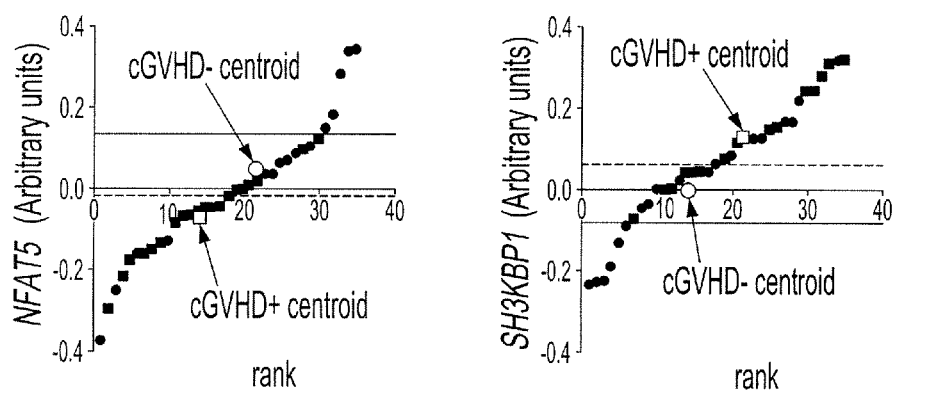
FIGS. 4A-4D: Competitive and synergistic interactions between GVHD-predictive genes.
Figure 4B:
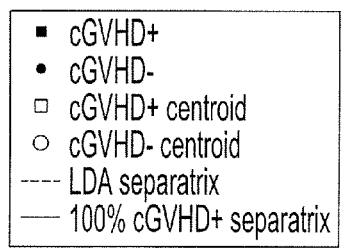
Figure 4C:
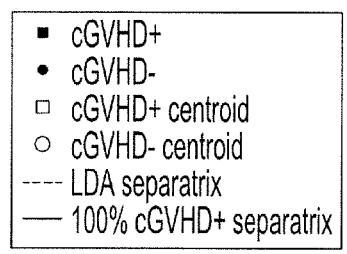
Figure 4D:
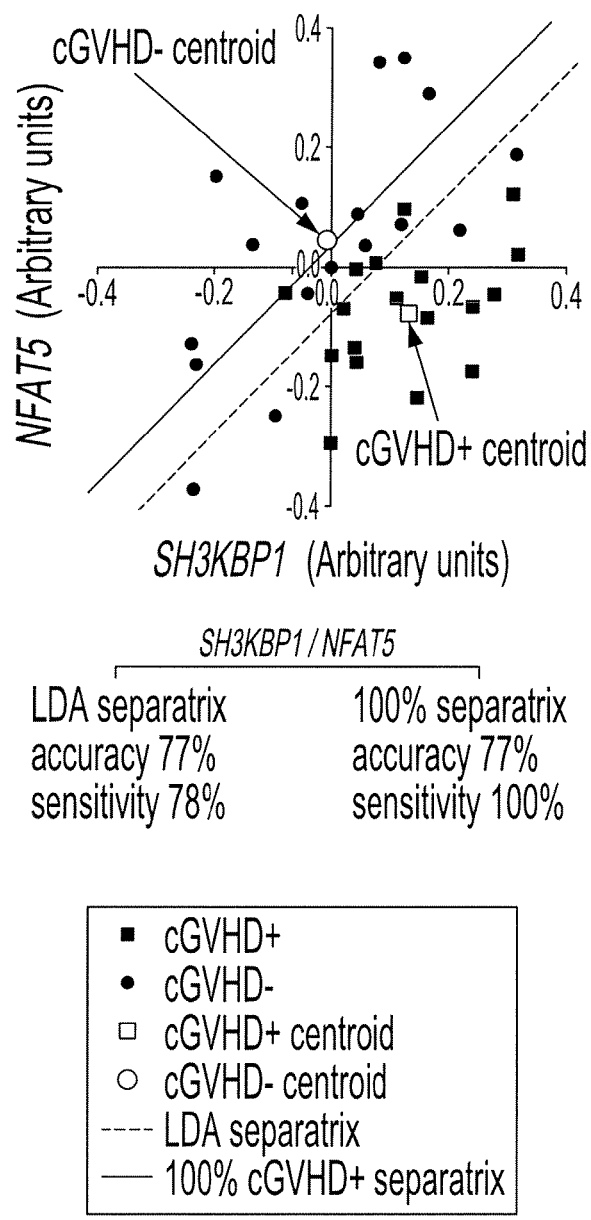

Applicant first carried out 8 searches using two methods, a statistical F-test and a specially constrained linear discriminant analysis (LDA) and four class divisions. Class divisions were for CD4$^+$ and CD8$^+$ T cells, i) recipients with no GVHD vs. those with aGVHD (with or without cGVHD), and ii) recipients with no GVHD vs. those with cGVHD (with or without aGVHD). Recipients were considered GVHD– only when they presented no signs of GVHD after a minimum follow-up of one year post-AHCT. Genes showing a GVHD– predictive LDA accuracy (ability to discriminate donors whose recipient presented GVHD or not) ≥65% and class discrimination F-test p-value≤0.05 (FIG. 2A) were selected for analysis. Further, it was found that many of the genes predictive for aGVHD were also predictive for cGVHD (FIG. 2B). A substantial proportion of GVHD-predictive genes were common to both CD4$^+$ and CD8$^+$ donor T cells (FIG. 2C). Since many GVHD-associated genes were found in only CD4$^+$ or CD8$^+$ T cells, in embodiments T-cell subsets may be analyzed independently (FIG. 2C). Among genes emerging from the ImmunArray and H19K datasets, those that are annotated and have a demonstrated or putative function in T-cell biology are listed in Table I. Overall, the numbers of genes whose expression was modulated (upregulated/downregulated) in GVHD+ relative to GVHD– donors were 22/42 for CD4$^+$ T cells and 31/40 for CD8$^+$ T cells. About 60% of these genes are involved in cell proliferation, signal transduction or gene transcription.

Example 4

Quantitative Real-Time RT-PCR (QRT-PCR) Analyses of GVHD– Predictive Genes

Predictive Value of Single Genes.

To evaluate the validity of predictive genes identified with microarrays, qRT-PCR analyses were performed on fresh mRNA aliquots extracted from donor CD4$^+$ (n=33) and CD8$^+$ (n=35) T cells. The analysis has been focused on cGVHD-predictive genes and a total of 26 genes were tested, including 24 genes present in Table I. The latter 24 genes were selected based on two criteria: they are involved in cell proliferation and/or cytokine signaling and were differentially expressed in cGVHD+ versus cGVHD− donors. Preliminary analysis of Table I showed that at least five cGVHD− predictive genes were components of the transforming growth factor-β (TGF-β) signaling pathway. These five genes were selected for quantitative PCR studies. To further evaluate the possible role of the TGF-β pathway, we also tested the expression of transforming growth β-induced factor (TGIF) and transforming growth factor, beta-induced, 68 kDa (TGFBI) (that were not present on the microarrays) because they are transcriptional targets of TGF-β. Performance of individual genes was evaluated using analysis of variance (ANOVA) and LDA. The statistical significance corresponds to ANOVA p-value whereas classification performance (overall accuracy, sensitivity and specificity) was derived from LDA. Sensitivity represents true positives/(true positives+false negatives), and specificity denotes true negatives/(true negatives+false positives).

Out of the 26 genes tested, 17 were differentially expressed in GVHD+ and GVHD− donors (Table II): 15 genes picked up from Table I (they showed consistent change-directionality in microarrays and qRT-PCR) plus the two added genes. The statistical significance (ANOVA p-value) of individual cGVHD-predictive genes ranged from 0.046 to 0.0008, and their GVHD-predictive accuracy (LDA) from 64 to 80% (Table II). Of note, there was a negative correlation ($r=-0.53$, $p=0.03$) between the specificity and sensitivity of the 17 genes. Thus, some genes were better in predicting the occurrence of GVHD than its absence, and vice versa for other genes. PRF1 showed the best specificity (Table II; FIG. 3). PRF1 codes for perforin whose high expression in $CD8^+$ T cells is associated with occurrence of GVHD. SMAD3, a transcription factor that is activated following TGF-β binding, showed the highest sensitivity (Table II; FIG. 3). High levels of SMAD3 transcripts in $CD4^+$ T cells correlated with absence of GVHD. Based on the LDA-generated class-separatrix the specificity and sensitivity for SMAD3 were 53% and 89% with an overall accuracy of 73%. We repositioned the separatrix in order to place all cGVHD+ donors on one side of the separatrix (hereafter referred to as the 100% cGVHD+ separatrix). This new separatrix, which by definition increased the sensitivity to 100%, also increased the overall accuracy to 79% without changing the specificity (FIG. 3). Thus low levels of SMAD3 were found in all GVHD+ and some GVHD− donors, while all donors expressing high levels of SMAD3 were GVHD− (FIG. 3). Mechanistically, this suggests that high levels of SMAD3 are sufficient (but not necessary) to prevent GVHD while low levels are necessary (but not sufficient) for the occurrence of GVHD.

In the studies described herein, it was found that all components and targets of the TGF-β pathway tested by qRT-PCR were differentially expressed in GVHD+ vs. GVHD− donors (Table II). Compared with GVHD+ donors, GVHD− donors showed upregulation of EP300, FURIN, FNBP3, SMAD3, TGFBI and TGIF, and repression of PRF1. The ten other cGVHD-predictive genes whose differential expression was confirmed by qRT-PCR are involved in regulation of cell growth and proliferation (AKT2, ATBF1, CD24, CD151, MYCL1, NFAT5, NMI, SIL, SH3KBP1, and TCIRG1) (Woodgett et al., (2005). Curr. Opin. Cell Biol. 17:150; Jung et al., (2005). Development 132:5137; Li et al., (2004). J. Exp. Med. 200:1083; Wright et al., (2004). Mol. Cell Biol. 24:5978; Ingvarsson, (1990). Semin. Cancer Biol. 1:359; Go et al., (2004). Proc. Natl. Acad. Sci. U.S.A 101:10673; Zhu et al., (1999). Cell 96:121; Aplan et al., (1991). Mol. Cell Biol. 11:5462; Soubeyran et al., (2002). Nature 416:183; Utku et al., (2004). J. Immunol. 173:2342).

Predictive Interaction Analyses Using a Pair-Wise Interaction Model.

In their simplest form, gene/gene interactions may be phenomenologically competitive or synergistic. We posited that such interactions might be reflected in particular gene pair expression patterns. For example, if gene X and gene Y represent a competitive interaction, the ratio of gene Y/X expression should determine GVHD outcome: presence and absence of GVHD will correlate with high and low Y/X ratios, respectively. Alternatively, for synergistic interactions, the occurrence of GVHD should be regulated by the product of genes X×Y. We therefore examined gene pair expression ratios and products within the context of competitive and synergistic models. To this end, we evaluated the gene pairs formed by the 15 GVHD-predictive genes validated in both microarray and qRT-PCR experiments (Table I and II). The total number of gene pairs analyzed corresponds to $N(N-1)/2$, i.e., 105. We asked whether competitive and synergistic predictive interaction analyses (CPIA and SPIA) would highlight gene pairs whose p-value for cGVHD prediction was at least tenfold lower than that of constituent genes. Four gene pairs satisfied this fairly stringent criterion (FIG. 4). PIAs suggest that NFAT5, a transcription factor that regulates gene expression induced by osmotic stress (Go et al., supra) has competitive interactions with SH3KBP1 (alias CIN85) that interacts with CBL (Soubeyran et al., supra) (a negative regulator of immune signaling), and with PRF1 a quintessential component of $CD8^+$ T-cell granule exocytosis cytotoxicity pathway (Barry et al., (2002). Nat. Rev. Immunol. 2:401). Likewise, PIAs suggest that PRF1 has competitive interactions with TCIRG1 (alias TIRC7) a negative regulator of T-cell activation and cytokine response (Utku et al., supra); and that CD151, a negative regulator of Ag-induced T-cell proliferation (Wright et al., supra), collaborates synergistically with SIL a gene whose expression is associated with cell proliferation (Erez et al., (2004). Oncogene 23:5371).

Gene pairs discovered by PIA can provide better performance than constituent single genes in terms of prediction accuracy. Performance gain is illustrated by further analyses of the SH3KBP1/NFAT5 gene pair using LDA and two class-separatrices: the LDA-generated separatrix and the 100% cGVHD+ separatrix (designed to maximize sensitivity) (FIG. 4). Compared to the LDA-generated separatrix, the 100% cGVHD+ separatrix increased the sensitivity by 22-39% without compromising overall accuracy (FIG. 4). Using the LDA-generated separatrix, the SH3KBP1/NFAT5 gene pair provided a 6% gain in sensitivity and 3% increment in overall accuracy compared with single genes. With the 100% cGVHD+ separatrix (that by definition gives a 100% sensitivity), the overall accuracy gain was 8%. From a clinical standpoint, these data suggest that PIAs can identify gene pairs with greatly enhanced predictive accuracies and p-values compared to their constituent genes. Furthermore, they imply and that in further studies including more subjects, higher-order combinatorial searches could significantly improve the prediction performance of gene expression profiling (Baranzini et al., (2005). PLoS. Biol. 3:e2).

Multiple Training-Test Dataset Split Cross-Validation.

Genes with good cGVHD+- and cGVHD−-differentiating t-test p-values over the complete set of samples have a statistically significant ability to distinguish between these classes (in terms of rejecting the equal means null hypothesis). The robust average accuracy over many independently generated test datasets for each gene was determined, on the basis of different selections of training-set data for each gene (Baranzini et al., supra), using conventional cross-validation procedures (Duda R O et al., (2001). Linear discriminant functions. In: Pattern classification New York: John Wiley & Sons, Inc. pp. 215-281). These analyses were performed on the 17 single genes (Table I) and the PIA variables representative of the four gene pairs (FIG. 4A) that were predictive of cGVHD occurrence. Specifically, for each gene, 500 different 60% training samples and 40% test-samples dataset splits were carried out by randomly assigning (for each data split) 60% of the respective cGVHD+ and cGVHD− samples to a training dataset, and the remaining 40% of the samples to the respective test datasets. For CD4+ cells, 11 cGVHD+ and nine cGVHD− samples were selected randomly for training datasets, while the seven cGVHD+ and six cGVHD− remaining samples were used in test datasets. For CD8+ cells, 11 cGVHD+ and ten cGVHD− samples were selected randomly for training datasets, while the remaining seven cGVHD+ and seven cGVHD− samples were used in test datasets. The test dataset accuracy was determined separately for each of the 500 training/test random-sampling splits by using the LDA-predictive model separatrix from the corresponding training dataset. Each test dataset-accuracy determination for each gene was carried out 500 separate times on randomly chosen dataset splits, each time using a predictive model that has never been exposed to the test data.

Figure 5:
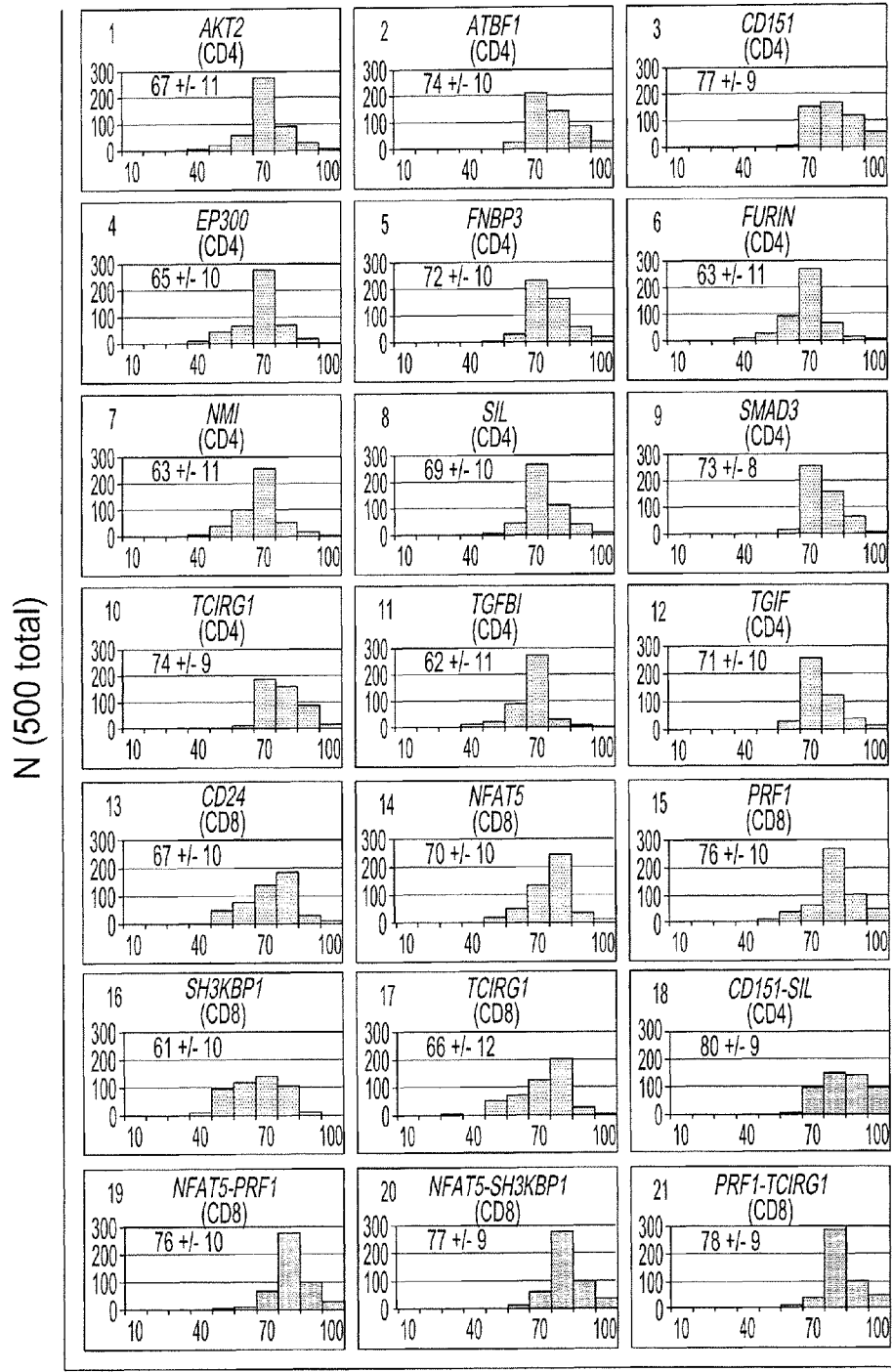
FIG. 5: Multiple Training-Test Dataset Split Cross-Validation. For each single gene (n=17; panels 1-17) and gene pairs (n=4, panels 18-21), 500 different 60% training samples and 40% test samples dataset splits were carried out by randomly assigning 60% of the respective cGVHD+ and cGVHD− samples to a training dataset and the remaining 40% of the samples to the respective test datasets. The test dataset accuracy was determined separately for each of the 500 training/test random sampling splits by using the LDA predictive model separatrix from the corresponding training dataset. Bar graphs show the occurrence of specific accuracies in 10% accuracy increments. Numbers within each graph represent the mean test-set accuracy (%)±standard deviation.

For each gene, the robust cross-validation ensemble average test-set accuracy and its standard deviation, as well as bar graphs depicting occurrences of specific accuracies in 10% accuracy increments is reported in FIG. 5. It was found that the average test-set cross-validation accuracy was 71%±10%, and that genes such as CD151 for CD4+ cells achieved an accuracy of 77%±9%, and PRF1 for CD8+ cells achieved 76%±10%. Notably, the test-set cross-validation accuracy of gene pairs identified by PIA often outperforms that of single genes. For example, the CD151-SIL gene pair achieved 80%±9%, while its constituent genes CD151 and SIL provided accuracies of 77%±9% and 69%±10%, respectively. In addition, FIG. 5 shows a conspicuous shift of occurrences of accuracies from the 70% and 80% histogram bins for the constituent genes to the 90% and 100% bins for the gene pairs. These data demonstrate that the 17 genes and four gene pairs reported herein not only show statistically significant differences between cGVHD+ and cGVHD− donors, but also that these differences are substantial in magnitude and robustly provide higher than 70% accuracies overall. Therefore, these genes and gene pairs are of particular clinical value for cGVHD prediction.

Example 5

The Microarray-Based Donor Gene Profile Persists Long-Term in the Recipient

Figure 6:
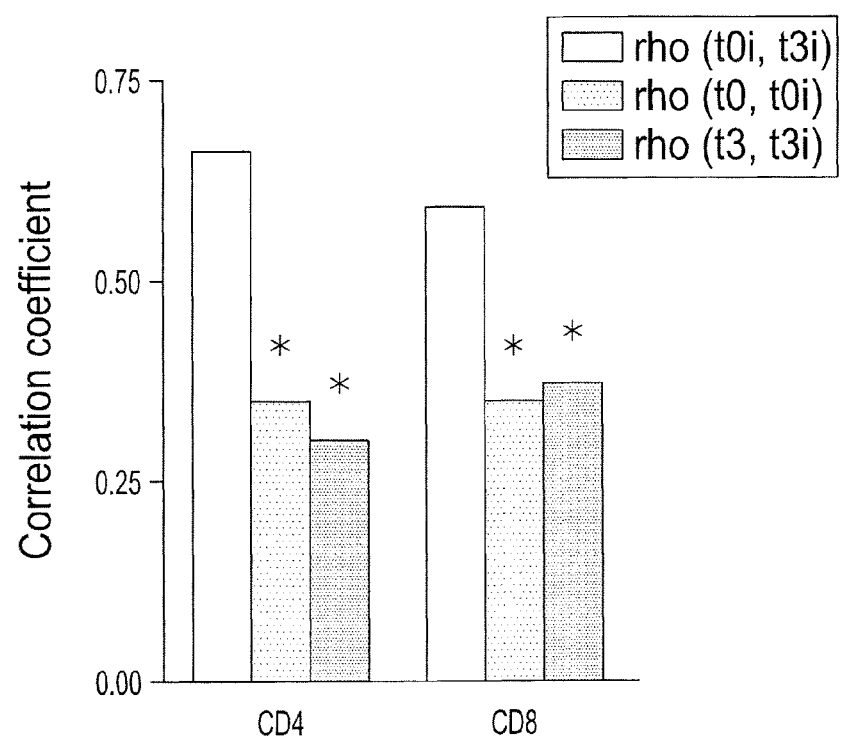
FIG. 6: The donor gene profile strongly impinges on the recipient profile examined one year post-AHCT. Histograms show average correlation between the expression profile (711 informative genes) of individual donors with their recipient (t0i-t3i, left bars); between individual donors and other donors on day 0 (t0i-t0, middle bars); and between individual recipients and other recipients on day 365 (t3i-t3, right bars). *p<10$^{-6}$ relative to (t0i-t3i). Data are from forty (40) donor-recipient pairs.

To further analyze the biological significance of differences in donor gene expression profiles we evaluated whether they persisted in the recipient. We therefore studied the relationship between the donor gene profiles on day 0 (t0) and the recipient profiles on day 365 (t3). To get a manageable yet broad basis for analyses, we included two gene sets tested on the H19K chip: the top 400 genes showing differential expression in GVHD+ vs. GVHD− donors on day 0, combined with the top 400 genes showing differential expression in GVHD+ vs. GVHD− recipients on day 365 (Table V). Because of overlap between the two gene sets, a total of 711 genes were analyzed. Genes that exhibited little variation across arrays were excluded because they do not contribute useful information for distinguishing among specimens (Miller et al., Cancer Cell 2:353). The basic postulate underlying our analyses was that if the donor profile is largely transferred to the recipient, correlation between a donor on day 0 and its recipient on day 365 (t0i-t3i) would be stronger than a) correlation of that donor with other donors on day 0 (t0i-t0) and b) correlation of that recipient with other recipients on day 365 (t3i-t3). The reverse would be true and the donor-specific characteristics should be "washed out" if adaptive changes in the recipients were strongly dominant. It was found that the average gene expression profile correlation among corresponding donor-recipient pairs (t0i-t3i) was consistently higher than the average correlation among donors (t0i-t0) ($p<10^{-6}$) and among recipients (t3i-t3) ($p<10^{-6}$). This was true both for CD4+ and CD8+ T cells (FIG. 6). Thus, the donor gene profile strongly impinges on the recipient profile examined one year post-AHCT.

TABLE I

Differential gene expression in GVHD+ and GVHD− donors.

| ImmunArray | | | | H19K | | | |
|---|---|---|---|---|---|---|---|
| CD4 | | CD8 | | CD4 | | CD8 | |
| aGVHD | | aGVHD | | aGVHD | | aGVHD | |
| NM_006564 | | NM_003240 | CDC42 | NM_005745 | BCAP31 | NM_001344 | DAD1 |
| NM_005900 | | NM_007051 | FAF1 | NM_001119 | ADD1 | NM_003974 | DOK2 |
| NM_006732 | | NM_006705 | GADD45G | NM_004281 | BAG3 | NM_012218 | ILF3 |
| NM_002758 | | NM_207585 | IFNAR2 | NM_015897 | PIAS4 | NM_006500 | MCAM |
| NM_002575 | SERPINB2 | NM_001550 | IFRD1 | NM_003376 | VEGF | NM_003721 | RFXANK |
| NM_003266 | TLR4 | NM_000597 | IGFBP2 | NM_003403 | YY1 | NM_005902 | SMAD3 |
| cGVHD | | NM_001571 | IRF3 | cGVHD | | NM_001066 | TNFRSF1B |
| NM_007051 | FAF1 | NM_002312 | LIG4 | NM_000877 | IL1R1 | NM_003376 | VEGF |
| NM_031892 | SH3KBP1 | NM_002755 | MAP2K1 | NM_006267 | RANBP2 | NM_003380 | VIM |
| NM_000732 | CD3D | NM_007289 | MME | NM_022807 | SNRPN | NM_003403 | YY1 |
| NM_012296 | GAB2 | NM_005739 | RASGRP1 | NM_144949 | SOCS5 | cGVHD | |
| NM_005456 | MAPK8IP1 | NM_007315 | STAT1 | NM_001626 | AKT2 | NM_001154 | ANXA5 |
| NM_005631 | SMO | NM_003234 | TFRC | NM_002569 | FURIN | NM_004356 | CD81 |
| aGVHD & cGVHD | | NM_006074 | TRIM22 | aGVHD & cGVHD | | NM_001827 | CKS2 |
| NM_001527 | HDAC2 | NM_001763 | CD1A | NM_001154 | ANXA5 | NM_002046 | GAPD |
| NM_000877 | IL1R1 | NM_000732 | CD3D | NM_001780 | CD63 | NM_000877 | IL1R1 |
| NM_004357 | CD151 | NM_172200 | IL15RA | NM_004356 | CD81 | NM_005376 | MYCL1 |
| NM_001429 | EP300 | NM_000206 | IL2RG | NM_001827 | CKS2 | NM_005983 | SKP2 |

TABLE I-continued

Differential gene expression in GVHD+ and GVHD− donors.

| ImmunArray | | | | H19K | | | |
|---|---|---|---|---|---|---|---|
| CD4 | | CD8 | | CD4 | | CD8 | |
| XM_371575 | FNBP3 | NM_181430 | 1LF1 | NM_001873 | CPE | NM_144949 | SOCS5 |
| NM_000565 | IL6R | NM_014387 | LAT | NM_002357 | MAD | aGVHD & cGVHD | |
| NM_004688 | NMI | NM_002412 | MGMT | NM_005376 | MYCL1 | NM_006112 | PPIE |
| NM_002611 | PDK2 | NM_003263 | TLR1 | NM_004208 | PDCD8 | NM_006325 | RAN |
| NM_015568 | PPP1R16B | cGVHD | | NM_001664 | RHOA | NM_006826 | YWHAQ |
| NM_003035 | SIL | NM_031892 | SH3KBP1 | NM_005983 | SKP2 | NM_004281 | BAG3 |
| NM_003089 | SNRP70 | NM_003222 | TFAP2C | NM_006826 | YWHAQ | NM_053056 | CCND1 |
| NM_007271 | STK38 | NM_002927 | RGS13 | NM_006885 | ATBF1 | NM_013230 | CD24 |
| NM_006019 | TCIRG1 | NM_003246 | THBS1 | NM_053056 | CCND1 | NM_021874 | CDC25B |
| | | aGVHD & cGVHD | | NM_021874 | CDC25B | NM_006387 | CHERP |
| | | NM_001789 | CDC25A | NM_006387 | CHERP | NM_003651 | CSDA |
| | | NM_000637 | GSR | NM_003651 | CSDA | NM_004394 | DAP |
| | | NM_005041 | PRF1 | NM_003974 | DOK2 | NM_001454 | FOXJ1 |
| | | NM_139205 | HDAC5 | NM_001454 | FOXJ1 | NM_002569 | FURIN |
| | | NM_138714 | NFAT5 | NM_000520 | HEXA | NM_002124 | HLA-DRB3 |
| | | NM_015897 | PIAS4 | NM_013995 | LAMP2 | NM_001540 | HSPB1 |
| | | NM_006019 | TCIRG1 | NM_006500 | MCAM | NM_013995 | LAMP2 |
| | | | | NM_002502 | NFKB2 | NM_002502 | NFKB2 |
| | | | | NM_000958 | PTGER4 | NM_002730 | PRKACA |
| | | | | NM_006325 | RAN | NM_000958 | PTGER4 |
| | | | | NM_003721 | RFXANK | | |
| | | | | NM_005902 | SMAD3 | | |
| | | | | NM_003380 | VIM | | |

GVHD-predictive genes identified by one-dimensional analyses of data from the ImmunArray and H19K chips. From genes with an F-test p-value $p \leq 0.05$ and LDA accuracy $\geq 65\%$ (FIG. 2), we listed those that are annotated and have a demonstrated or putative function in T-cell biology.
Genes overexpressed and repressed in GVHD+ relative to GVHD− donors are in bold and standard print, respectively.

TABLE II qRT-PCR analyses of GVHD-predictive genes.

| Gene | Cell Type | qRT-PCR cGVHD+ vs. cGVHD− p-value | Specificity | Sensitivity | Accuracy |
|---|---|---|---|---|---|
| TCIRG1 | CD4 | 0.0008 | 73% | 78% | 76% |
| SMAD3 | CD4 | 0.0012 | 53% | 89% | 73% |
| ATBF1 | CD4 | 0.0018 | 67% | 83% | 76% |
| AKT2 | CD4 | 0.0023 | 67% | 72% | 70% |
| CD24 | CD8 | 0.0027 | 65% | 72% | 69% |
| CD151 | CD4 | 0.0030 | 73% | 78% | 76% |
| TGIF* | CD4 | 0.0031 | 60% | 83% | 73% |
| SIL | CD4 | 0.0036 | 60% | 83% | 73% |
| PRF1 | CD8 | 0.0039 | 88% | 72% | 80% |
| FNBP3 | CD4 | 0.0045 | 60% | 83% | 73% |
| TGFBI* | CD4 | 0.0048 | 67% | 61% | 64% |
| EP300 | CD4 | 0.0061 | 47% | 78% | 64% |
| SH3KBP1 | CD8 | 0.0067 | 65% | 61% | 63% |
| NMI | CD4 | 0.0092 | 60% | 67% | 64% |
| FURIN | CD4 | 0.0105 | 73% | 56% | 64% |
| NFAT5 | CD8 | 0.0222 | 71% | 72% | 71% |
| TCIRG1 | CD8 | 0.0460 | 76% | 56% | 66% |
| STK38, IL1R1, PDCD8, FAF1, IL6R, MYCL1, SH3KBP1, RAN | CD4 | NS | | | |
| RAN | CD8 | NS | | | |

Genes overexpressed and repressed in cGVHD+ relative to cGVHD− donors are in bold and standard print, respectively.
The seven genes underlined are components and targets of the TGF-β signaling pathway.
Two TGF-β target genes that were not represented on the microarrays are labeled with an asterisk.
NS, not significant by qRT-PCR. Specificity = true negatives/(true negatives + false positives); sensitivity = true positives/(true positives + false negatives).

TABLE III

Correspondence of SEQ ID NOs: of sequences described herein.

| Accession Number | Gene name | SEQ ID No (nucleotide) | SEQ ID No (polypeptide) | Accession Number | Gene name | SEQ ID No (nucleotide) | SEQ ID No (polypeptide) |
| --- | --- | --- | --- | --- | --- | --- | --- |
| NM_006564 | CXCR6 | 1 | 2 | NM_000565 | IL6R | 105 | 106 |
| NM_005900 | SMAD1 | 3 | 4 | NM_004688 | NMI | 107 | 108 |
| NM_007051 | FAF1 | 5 | 6 | NM_002611 | PDK2 | 109 | 110 |
| NM_031892 | SH3KBP1 | 7 | 8 | NM_015568 | PPP1R16B | 111 | 112 |
| NM_001527 | HDAC2 | 9 | 10 | NM_003035 | SIL | 113 | 114 |
| NM_000877 | IL1R1 | 11 | 12 | NM_003089 | SNRP70 | 115 | 116 |
| NM_003240 | CDC42 | 13 | 14 | NM_007271 | STK38 | 117 | 118 |
| NM_006705 | GADD45G | 15 | 16 | NM_006019 | TCIRG1 | 119 | 120 |
| NM_207585 | IFNAR2 | 17 | 18 | NM_001763 | CD1A | 121 | 122 |
| NM_001550 | IFRD1 | 19 | 20 | NM_172200 | IL15RA | 123 | 124 |
| NM_000597 | IGFBP2 | 21 | 22 | NM_000206 | IL2RG | 125 | 126 |
| NM_001571 | IRF3 | 23 | 24 | NM_181430 | ILF1 | 127 | 128 |
| NM_002312 | LIG4 | 25 | 26 | NM_014387 | LAT | 129 | 130 |
| NM_002755 | MAP2K1 | 27 | 28 | NM_002412 | MGMT | 131 | 132 |
| NM_007289 | MME | 29 | 30 | NM_003263 | TLR1 | 133 | 134 |
| NM_005739 | RASGRP1 | 31 | 32 | NM_002927 | RGS13 | 135 | 136 |
| NM_007315 | STAT1 | 33 | 34 | NM_003246 | THBS1 | 137 | 138 |
| NM_003234 | TFRC | 35 | 36 | NM_138714 | NFAT5 | 139 | 140 |
| NM_006074 | TRIM22 | 37 | 38 | NM_015897 | PIAS4 | 141 | 142 |
| NM_003222 | TFAP2C | 39 | 40 | NM_001119 | ADD1 | 143 | 144 |
| NM_001789 | CDC25A | 41 | 42 | NM_004281 | BAG3 | 145 | 146 |
| NM_000637 | GSR | 43 | 44 | NM_003376 | VEGF | 147 | 148 |
| NM_005041 | PRF1 | 45 | 46 | NM_003403 | YY1 | 149 | 150 |
| NM_005745 | BCAP31 | 47 | 48 | NM_001626 | AKT2 | 151 | 152 |
| NM_006267 | RANBP2 | 49 | 50 | NM_002569 | FURIN | 153 | 154 |
| NM_022885 | SNRPN | 51 | 52 | NM_006885 | ATBF1 | 155 | 156 |
| NM_144949 | SOCS5 | 53 | 54 | NM_053056 | CCND1 | 157 | 158 |
| NM_001154 | ANXA5 | 55 | 56 | NM_006387 | CHERP | 159 | 160 |
| NM_001780 | CD63 | 57 | 58 | NM_003651 | CSDA | 161 | 162 |
| NM_004356 | CD81 | 59 | 60 | NM_003974 | DOK2 | 163 | 164 |
| NM_001827 | CKS2 | 61 | 62 | NM_001454 | FOXJ1 | 165 | 166 |
| NM_001873 | CPE | 63 | 64 | NM_000520 | HEXA | 167 | 168 |
| NM_002357 | MAD | 65 | 66 | NM_013995 | LAMP2 | 169 | 170 |
| NM_005376 | MYCL1 | 67 | 68 | NM_006500 | MCAM | 171 | 172 |
| NM_004208 | PDCD8 | 69 | 70 | NM_002502 | NFKB2 | 173 | 174 |
| NM_001664 | RHOA | 71 | 72 | NM_000958 | PTGER4 | 175 | 176 |
| NM_005983 | SKP2 | 73 | 74 | NM_001344 | DAD1 | 177 | 178 |
| NM_006826 | YWHAQ | 75 | 76 | NM_012218 | ILF3 | 179 | 180 |
| NM_002046 | GAPD | 77 | 78 | NM_003721 | RFXANK | 181 | 182 |
| NM_006112 | PPIE | 79 | 80 | NM_005902 | SMAD3 | 183 | 184 |
| NM_006325 | RAN | 81 | 82 | NM_001066 | TNFRSF1B | 185 | 186 |
| NM_006732 | FOSB | 83 | 84 | NM_003380 | VIM | 187 | 188 |
| NM_002758 | MAP2K6 | 85 | 86 | NM_013230 | CD24 | 189 | 190 |
| NM_002575 | SERPINB2 | 87 | 88 | NM_004394 | DAP | 191 | 192 |
| NM_003266 | TLR4 | 89 | 90 | NM_002124 | HLA-DRB1 | 193 | 194 |
| NM_000732 | CD3D | 91 | 92 | NM_001540 | HSPB1 | 195 | 196 |
| NM_012296 | GAB2 | 93 | 94 | NM_002730 | PRKACA | 197 | 198 |
| NM_005456 | MAPK8IP1 | 95 | 96 | NM_139205 | HDAC5 | 199 | 200 |
| NM_005631 | SMO | 97 | 98 | NM_021874 | CDC25B | 201 | 202 |
| NM_004357 | CD151 | 99 | 100 | NM_003244 | TGIF | 203 | 204 |
| NM_001429 | EP300 | 101 | 102 | NM_000358 | TGFBI | 205 | 206 |
| XM_371575 | FNBP3 | 103 | 104 | | | | |

TABLE IV

Results of expression analysis in GVHD+ and GVHD− samples.

| Gene | Cell Type | qRT-PCR cGVHD threshold value | RQ | Expression level/threshold if good donor |
| --- | --- | --- | --- | --- |
| TCIRG1 | CD4 | 114.28 | | higher |
| SMAD3 | CD4 | 3.98 | | higher |
| ATBF1 | CD4 | 0.34 | | higher |
| AKT2 | CD4 | 38.79 | | higher |
| CD24 | CD8 | 2.25 | | higher |
| CD151 | CD4 | 0.55 | | higher |
| TGIF* | CD4 | 2.03 | | higher |
| SIL | CD4 | 0.15 | | higher |
| PRF1 | CD8 | 1.26 | | lower |
| FNBP3 | CD4 | 1.86 | | higher |
| TGFBI* | CD4 | 5.56 | | higher |
| EP300 | CD4 | 9.37 | | higher |
| SH3KBP1 | CD8 | 1.17 | | lower |
| NMI | CD4 | 4.44 | | higher |

TABLE IV-continued

Results of expression analysis in GVHD+ and GVHD− samples.

| Gene | Cell Type | qRT-PCR cGVHD threshold value | RQ | Expression level/threshold if good donor |
|---|---|---|---|---|
| FURIN | CD4 | 0.30 | | higher |
| NFAT5 | CD8 | 1.03 | | higher |
| TCIRG1 | CD8 | 2.85 | | higher |

Genes overexpressed and repressed in cGVHD+ relative to cGVHD− donors are in bold and standard print, respectively.
The seven genes underlined are components and targets of the TGF-β signaling pathway.
Two TGF-β target genes that were not represented on the microarrays are labeled with an asterisk.
Relative quantification of target genes was determined by using the ΔΔCT method.
Relative expression (RQ) was calculated using reference RNA and a normal individual for CD4+ and CD8+, respectively.

TABLE V

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

day 0

00018-EPHB2-EphB2
00055-API5-apoptosis inhibitor 5
00078-RAN-RAN, member RAS oncogene family
00126-RAB25-RAB25, member RAS oncogene family
00144-GNG13-guanine nucleotide binding protein (G protein), gamma 13
00148-MGC35285-hypothetical protein MGC35285
00248-FMNL1-formin-like 1
00288-PSMA5-proteasome (prosome, macropain) subunit, alpha type, 5
00346-BAG3-BCL2-associated athanogene 3
00504-SOCS5-suppressor of cytokine signaling 5
00551-AKT2-v-akt murine thymoma viral oncogene homolog 2
00565-GAB1-GRB2-associated binding protein 1
00606-MT1G-metallothionein 1G
00666-TSBF1-tumor suppressor TSBF1
00671-FLJ12985-hypothetical protein FLJ12985
00692-SMAD3-MAD, mothers against decapentaplegic homolog 3 (Drosophila)
00734-XPO7-exportin 7
00918-GULP1-GULP, engulfment adaptor PTB domain containing 1
00942-GRCA-likely ortholog of mouse gene rich cluster, A gene
00956-FBLP-1-filamin-binding LIM protein-1
00983-CKS2-CDC28 protein kinase regulatory subunit 2
01070-ANXA5-annexin A5
01100-TPM4-tropomyosin 4
01157-ATP6V1G1-ATPase, H+ transporting, lysosomal 13 kDa, V1 subunit G isoform 1
01193-RPS28-ribosomal protein S28
01210-SPARC-secreted protein, acidic, cysteine-rich (osteonectin)
01213-TFEB-transcription factor EB
01278-SSB-Sjogren syndrome antigen B (autoantigen La)
01306-DLX4-distal-less homeobox 4
01307-ST18-suppression of tumorigenicity 18 (breast carcinoma) (zinc finger protein)
01386-PSMC4-proteasome (prosome, macropain) 26S subunit, ATPase, 4
01431-FES-feline sarcoma oncogene
01434-SIPA1-signal-induced proliferation-associated gene 1
01483-CCT6A-chaperonin containing TCP1, subunit 6A (zeta 1)
01499-CCNB2-cyclin B2
01515-RPE-ribulose-5-phosphate-3-epimerase
01715-RECK-reversion-inducing-cysteine-rich protein with kazal motifs
01721-IFITM1-interferon induced transmembrane protein 1 (9-27)
01723-CD79A-CD79A antigen (immunoglobulin-associated alpha)
01817-PHEMX-pan-hematopoietic expression
01839-MAD-MAX dimerization protein 1
01913-RHBDL2-rhomboid, veinlet-like 2 (Drosophila)
02007-GTPBP5-GTP binding protein 5 (putative)
02043-NKIRAS2-NFKB inhibitor interacting Ras-like protein 2
02091-PDCD8-programmed cell death 8 (apoptosis-inducing factor)
02094-PSG9-pregnancy specific beta-1-glycoprotein 9
02186-GRWD1-glutamate-rich WD repeat containing 1
02193-KRT8-keratin 8
02240-CSNK2B-casein kinase 2, beta polypeptide
02358-ITGB4-integrin, beta 4
02368-MYCL1-v-myc myelocytomatosis viral oncogene homolog 1, lung carcinoma derived (avian)
02410-RGN-regucalcin (senescence marker protein-30)
02412-TLN2-talin 2
02484-PILRB-paired immunoglobin-like type 2 receptor beta
02502-ANK3-ankyrin 3, node of Ranvier (ankyrin G)
02509-HDGF-hepatoma-derived growth factor (high-mobility group protein 1-like)

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

02567-PIGT-phosphatidylinositol glycan, class T
02580-RHO-rhodopsin (opsin 2, rod pigment) (retinitis pigmentosa 4, autosomal dominant)
02628-SENP7-SUMO1/sentrin specific protease 7
02662-HBB-hemoglobin, beta
02666-SPUVE-protease, serine, 23
02720-DHCR24-24-dehydrocholesterol reductase
02752-KDELR1-KDEL (Lys-Asp-Glu-Leu) endoplasmic reticulum protein retention receptor 1
02760-KAI1-kangai 1 (suppression of tumorigenicity 6, prostate; CD82 antigen
(R2 leukocyte antigen, antigen detected by monoclonal and antibody IA4))
02786-ATP5O-ATP synthase, H+ transporting, mitochondrial F1 complex,
O subunit (oligomycin sensitivity conferring protein)
02844-COG7-component of oligomeric golgi complex 7
02901-M6PRBP1-mannose-6-phosphate receptor binding protein 1
02935-MBD3-methyl-CpG binding domain protein 3
02993-ELP3-elongation protein 3 homolog (S. cerevisiae)
03007-MT2A-metallothionein 2A
03031-GSR-glutathione reductase
03077-MTPN-myotrophin
03256-ZNF291-zinc finger protein 291
03262-SEC24A-SEC24 related gene family, member A (S. cerevisiae)
03330-PIASY-protein inhibitor of activated STAT protein PIASy
03343-MGAT3-mannosyl (beta-1,4-)-glycoprotein beta-1,4-N-acetylglucosaminyltransferase
03430-TAF13-TAF13 RNA polymerase II, TATA box binding protein (TBP)-associated factor, 18 kDa
03443-TRIM32-tripartite motif-containing 32
03467-ANXA4-annexin A4
03481-GFAP-glial fibrillary acidic protein
03484-MARS-methionine-tRNA synthetase
03560-RAI3-retinoic acid induced 3
03604-MYOHD1-myosin head domain containing 1
03676-CALM2-calmodulin 2 (phosphorylase kinase, delta)
03705-ZN F-kaiso-kaiso
03759-COX5A-cytochrome c oxidase subunit Va
03770-ILF3-interleukin enhancer binding factor 3, 90 kDa
03808-ACADSB-acyl-Coenzyme A dehydrogenase, short/branched chain
03825-RAB13-RAB13, member RAS oncogene family
03896-DNASE2-deoxyribonuclease II, lysosomal
03898-PRDX4-peroxiredoxin 4
03917-TNFRSF7-tumor necrosis factor receptor superfamily, member 7
03927-ATF6-activating transcription factor 6
03928-PPIE-peptidylprolyl isomerase E (cyclophilin E)
03945-TNFRSF1B-tumor necrosis factor receptor superfamily, member 1B
04012-LAMP2-lysosomal-associated membrane protein 2
04072-COL6A1-collagen, type VI, alpha 1
04131-ANXA5-annexin A5
04145-SLC6A1-solute carrier family 6 (neurotransmitter transporter, GABA), member 1
04151-CD24-CD24 antigen (small cell lung carcinoma cluster 4 antigen)
04209-RAB26-RAB26, member RAS oncogene family
04296-GPSN2-glycoprotein, synaptic 2
04354-THRAP6-thyroid hormone receptor associated protein 6
04370-MPG-N-methylpurine-DNA glycosylase
04418-GRP58-glucose regulated protein, 58 kDa
04434-CENTA1-centaurin, alpha 1
04550-ATBF1-AT-binding transcription factor 1
04601-APEX2-APEX nuclease (apurinic/apyrimidinic endonuclease) 2
04721-ASMTL-acetylserotonin O-methyltransferase-like
04842-NDRG3-NDRG family member 3
04924-RNH-ribonuclease/angiogenin inhibitor
04941-TRPV6-transient receptor potential cation channel, subfamily V, member 6
04993-ROCK1-Rho-associated, coiled-coil containing protein kinase 1
05008-GMNN-geminin, DNA replication inhibitor
05138-PRKAR1B-protein kinase, cAMP-dependent, regulatory, type I, beta
05195-EBI2-Epstein-Barr virus induced gene 2 (lymphocyte-specific G protein-coupled receptor)
05232-CD63-CD63 antigen (melanoma 1 antigen)
05314-SNAP23-synaptosomal-associated protein, 23 kDa
05407-MPHOSPH1-M-phase phosphoprotein 1
05484-CSRP2-cysteine and glycine-rich protein 2
05506-AHSG-alpha-2-HS-glycoprotein
05554-HSD11B1-hydroxysteroid (11-beta) dehydrogenase 1
05587-EPLIN-epithelial protein lost in neoplasm beta
05652-TM6SF1-transmembrane 6 superfamily member 1
05664-TOMM20-translocase of outer mitochondrial membrane 20 homolog (yeast)
05666-RAD23B-RAD23 homolog B (S. cerevisiae)
05674-CKLF-chemokine-like factor
05721-GPX3-glutathione peroxidase 3 (plasma)
05763-BST1-bone marrow stromal cell antigen 1

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

05823-FER1L3-fer-1-like 3, myoferlin (C. elegans)
06001-GTF3C4-general transcription factor IIIC, polypeptide 4, 90 kDa
06060-TMEM8-transmembrane protein 8 (five membrane-spanning domains)
06080-ATP13A-ATPase type 13A
06148-RAB9P40-Rab9 effector p40
06149-CD81-CD81 antigen (target of antiproliferative antibody 1)
06177-SNRPN-small nuclear ribonucleoprotein polypeptide N
06315-KPTN-kaptin (actin binding protein)
06352-PDE7B-phosphodiesterase 7B
06380-GAPD-glyceraldehyde-3-phosphate dehydrogenase
06412-USP28-ubiquitin specific protease 28
06465-APOC1-apolipoprotein C-I
06497-PGPEP1-pyroglutamyl-peptidase I
06549-CEP2-centrosomal protein 2
06560-PEPD-peptidase D
06565-SAE1-SUMO-1 activating enzyme subunit 1
06568-TMEM1-transmembrane protein 1
06593-ROCK1-Rho-associated, coiled-coil containing protein kinase 1
06608-GMNN-geminin, DNA replication inhibitor
06664-MGC13138-hypothetical protein MGC13138
06818-XPR1-xenotropic and polytropic retrovirus receptor
06879-NEDL1-HECT type E3 ubiquitin ligase
07003-PRKACA-protein kinase, cAMP-dependent, catalytic, alpha
07028-PRKAA1-protein kinase, AMP-activated, alpha 1 catalytic subunit
07129-HLA-DRB3-major histocompatibility complex, class II, DR beta 3
07151-IL1R1-interleukin 1 receptor, type I
07211-NCOR1-nuclear receptor co-repressor 1
07346-RAB6A-RAB6A, member RAS oncogene family
07357-TCF7L1-transcription factor 7-like 1 (T-cell specific, HMG-box)
07359-NUMA1-nuclear mitotic apparatus protein 1
07366-CAMKK1-calcium/calmodulin-dependent protein kinase kinase 1, alpha
07408-AGMAT-agmatine ureohydrolase (agmatinase)
07469-VIM-vimentin
07508-NR2F2-nuclear receptor subfamily 2, group F, member 2
07520-ACTR1B-ARP1 actin-related protein 1 homolog B, centractin beta (yeast)
07568-SC4MOL-sterol-C4-methyl oxidase-like
07569-SAS-sarcoma amplified sequence
07598-DHCR24-24-dehydrocholesterol reductase
07599-RAB2-RAB2, member RAS oncogene family
07602-YWHAQ-tyrosine 3-monooxygenase/tryptophan 5-monooxygenase activation protein, theta polypeptide
07704-HOXB5-homeo box B5
07776-NFKB2-nuclear factor of kappa light polypeptide gene enhancer in B-cells 2 (p49/p100)
07781-CD68-CD68 antigen
07812-DAP-death-associated protein
07828-PTGER4-prostaglandin E receptor 4 (subtype EP4)
07835-PSMB4-proteasome (prosome, macropain) subunit, beta type, 4
07926-MINK-misshapen/NIK-related kinase
07950-SSRP1-structure specific recognition protein 1
08141-EPB49-erythrocyte membrane protein band 4.9 (dematin)
08197-CYP39A1-cytochrome P450, family 39, subfamily A, polypeptide 1
08257-QRSL1-glutaminyl-tRNA synthase (glutamine-hydrolyzing)-like 1
08346-POLR2J-polymerase (RNA) II (DNA directed) polypeptide J, 13.3 kDa
08417-TAGLN2-transgelin 2
08434-MORF4L1-mortality factor 4 like 1
08512-TREX1-three prime repair exonuclease 1
08568-LOC124245-hypothetical protein BC001584
08778-TBCD-tubulin-specific chaperone d
08877-RNPEPL1-arginyl aminopeptidase (aminopeptidase B)-like 1
08942-DNM1-dynamin 1
08974-UAP1-UDP-N-acteylglucosamine pyrophosphorylase 1
09016-TGFBRAP1-transforming growth factor, beta receptor associated protein 1
09069-VIM-vimentin
09112-SEL1L-sel-1 suppressor of lin-12-like (C. elegans)
09117-ADH6-alcohol dehydrogenase 6 (class V)
09132-RPL31-ribosomal protein L31
09137-EIF4G2-eukaryotic translation initiation factor 4 gamma, 2
09159-VRK3-vaccinia related kinase 3
09177-C6orf69-chromosome 6 open reading frame 69
09206-MOBP-myelin-associated oligodendrocyte basic protein
09232-CD63-CD63 antigen (melanoma 1 antigen)
09278-PGPL-pseudoautosomal GTP-binding protein-like
09291-ZNF205-zinc finger protein 205
09304-RAB40C-RAB40C, member RAS oncogene family
09397-PDE2A-phosphodiesterase 2A, cGMP-stimulated
09488-TGOLN2-trans-golgi network protein 2

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

09497-FOXJ1-forkhead box J1
09503-KNS2-kinesin 2 60/70 kDa
09571-TPM1-tropomyosin 1 (alpha)
09678-TMEM9-transmembrane protein 9
09878-VEGF-vascular endothelial growth factor
09911-CYP4F12-cytochrome P450, family 4, subfamily F, polypeptide 12
10053-JPH3-junctophilin 3
10071-FKSG44-hypothetical protein FKSG44
10114-TCEB3BP1-transcription elongation factor B polypeptide 3 binding protein 1
10164-LOC132241-hypothetical protein LOC132241
10213-RAMP3-receptor (calcitonin) activity modifying protein 3
10260-BCAP31-B-cell receptor-associated protein 31
10266-APOB-apolipoprotein B (including Ag(x) antigen)
10272-RRAGD-Ras-related GTP binding D
10295-IGFBP6-insulin-like growth factor binding protein 6
10461-SNRPD3-small nuclear ribonucleoprotein D3 polypeptide 18 kDa
10542-SYT5-synaptotagmin V
10564-SCML1-sex comb on midleg-like 1 (*Drosophila*)
10597-MCM3AP-MCM3 minichromosome maintenance deficient 3 (*S. cerevisiae*) associated protein
10600-SOX12-SRY (sex determining region Y)-box 12
10630-PPARD-peroxisome proliferative activated receptor, delta
10650-MBNL2-muscleblind-like 2 (*Drosophila*)
10832-CAPN10-calpain 10
10874-CARD14-caspase recruitment domain family, member 14
10877-CBFA2T2-core-binding factor, runt domain, alpha subunit 2; translocated to, 2
10987-PRG2-proteoglycan 2, bone marrow (natural killer cell activator, eosinophil granule major basic protein)
11001-C20orf121-chromosome 20 open reading frame 121
11023-RFXANK-regulatory factor X-associated ankyrin-containing protein
11029-DKFZP566E144-small fragment nuclease
11091-HEXA-hexosaminidase A (alpha polypeptide)
11107-UBE2H-ubiquitin-conjugating enzyme E2H (UBC8 homolog, yeast)
11126-DDX54-DEAD (Asp-Glu-Ala-Asp) box polypeptide 54
11127-GGTLA1-gamma-glutamyltransferase-like activity 1
11154-TEAD1-TEA domain family member 1 (SV40 transcriptional enhancer factor)
11162-HS3ST4-heparan sulfate (glucosamine) 3-O-sulfotransferase 4
11200-HCRTR1-hypocretin (orexin) receptor 1
11243-TIPARP-TCDD-inducible poly(ADP-ribose) polymerase
11263-MASP1-mannan-binding lectin serine protease 1 (C4/C2 activating component of Ra-reactive factor)
11332-FLJ11856-putative G-protein coupled receptor GPCR41
11333-RGS12-regulator of G-protein signalling 12
11352-NEUROD6-neurogenic differentiation 6
11381-RHOT1-ras homolog gene family, member T1
11409-MYL4-myosin, light polypeptide 4, alkali; atrial, embryonic
11467-SPUVE-protease, serine, 23
11484-HSPB1-heat shock 27 kDa protein 1
11539-CSTB-cystatin B (stefin B)
11554-SLC2A10-solute carrier family 2 (facilitated glucose transporter), member 10
11742-CHERP-calcium homeostasis endoplasmic reticulum protein
11784-ZF-HCF-binding transcription factor Zhangfei
11787-F2-coagulation factor II (thrombin)
11796-HEL308-DNA helicase HEL308
11807-DUSP22-dual specificity phosphatase 22
11824-CSDA-cold shock domain protein A
11826-SNX15-sorting nexin 15
11902-CDH11-cadherin 11, type 2, OB-cadherin (osteoblast)
11928-IL1R1-interleukin 1 receptor, type I
12071-TM4SF8-transmembrane 4 superfamily member 8
12121-SLC27A1-solute carrier family 27 (fatty acid transporter), member 1
12155-DNB5-deleted in neuroblastoma 5
12188-TERE1-transitional epithelia response protein
12210-RANBP2-RAN binding protein 2
12221-APOE-apolipoprotein E
12282-RFC4-replication factor C (activator 1) 4, 37 kDa
12350-PAPSS1-3'-phosphoadenosine 5'-phosphosulfate synthase 1
12355-COL18A1-collagen, type XVIII, alpha 1
12357-CAV1-caveolin 1, caveolae protein, 22 kDa
12378-ARGBP2-Arg/Abl-interacting protein ArgBP2
12425-IMPA2-inositol(myo)-1(or 4)-monophosphatase 2
12493-GABARAP-GABA(A) receptor-associated protein
12569-ZAK-sterile alpha motif and leucine zipper containing kinase AZK
12599-SULT1E1-sulfotransferase family 1E, estrogen-preferring, member 1
12624-P2RX7-purinergic receptor P2X, ligand-gated ion channel, 7
12627-SOX4-SRY (sex determining region Y)-box 4
12629-LASP1-LIM and SH3 protein 1
12639-CSNK2B-casein kinase 2, beta polypeptide TABLE V-continued Gene sets used to evaluate the correlation between the donor and recipient gene expression profiles. The gene sets include the top 400 genes showing differential expression in GVHD+ vs. GVHD– donors on day 0, combined with the top 400 genes showing differential expression in GVHD+ vs. GVHD– recipients on day 365.

12729-SCARB1-scavenger receptor class B, member 1
12799-TNXB-tenascin XB
12859-Cbx5-chromobox homolog 5 (*Drosophila* HP1a)
12881-MK167IP-MK167 (FHA domain) interacting nucleolar phosphoprotein
12988-ERCC1-excision repair cross-complementing rodent repair deficiency, complementation group 1 (includes overlapping antisense sequence)
13035-MCC-mutated in colorectal cancers
13350-NPC2-Niemann-Pick disease, type C2
13393-PARG-poly (ADP-ribose) glycohydrolase
13547-TRIM29-tripartite motif-containing 29
13552-DAD1-defender against cell death 1
13617-YY1-YY1 transcription factor
13709-PCBP1-poly(rC) binding protein 1
13750-LOC221955-KCCR13L
13757-RALB-v-ral simian leukemia viral oncogene homolog B (ras related; GTP binding protein)
13771-QSCN6L1-quiescin Q6-like 1
13866-FN1-fibronectin 1
14005-MGC24039-hypothetical protein MGC24039
14042-RBM8A-RNA binding motif protein 8A
14177-LONP-peroxisomal lon protease
14178-DPP6-dipeptidylpeptidase 6
14291-NSEP1-nuclease sensitive element binding protein 1
14296-PLTP-phospholipid transfer protein
14300-PILRB-paired immunoglobin-like type 2 receptor beta
14356-POU2F1-POU domain, class 2, transcription factor 1
14486-SLC4A5-solute carrier family 4, sodium bicarbonate cotransporter, member 5
14528-DUSP1-dual specificity phosphatase 1
14549-EVI5-ecotropic viral integration site 5
14623-ATP5G3-ATP synthase, H+ transporting, mitochondrial F0 complex, subunit c (subunit 9) isoform 3
14628-MAN2A2-mannosidase, alpha, class 2A, member 2
14665-PNUTL2-peanut-like 2 (*Drosophila*)
14696-BSPRY-B-box and SPRY domain containing
14825-NME1-non-metastatic cells 1, protein (NM23A) expressed in
14941-RPS28-ribosomal protein S28
14944-CELSR2-cadherin, EGF LAG seven-pass G-type receptor 2 (flamingo homolog, *Drosophila*)
15027-CCND1-cyclin D1 (PRAD1: parathyroid adenomatosis 1)
15028-CIAO1-WD40 protein Ciao 1
15079-ARPP-19-cyclic AMP phosphoprotein, 19 kD
15148-SLC25A5-solute carrier family 25 (mitochondrial carrier; adenine nucleotide translocator), member 5
15216-UNC5A-unc-5 homolog A (*C. elegans*)
15229-NUP155-nucleoporin 155 kDa
15313-SKP2-S-phase kinase-associated protein 2 (p45)
15322-CD79B-CD79B antigen (immunoglobulin-associated beta)
15341-ADORA1-adenosine A1 receptor
15346-IDS-iduronate 2-sulfatase (Hunter syndrome)
15363-CTSE-cathepsin E
15416-ADD1-adducin 1 (alpha)
15440-SQRDL-sulfide quinone reductase-like (yeast)
15461-DOK2-docking protein 2, 56 kDa
15562-CDC25B-cell division cycle 25B
15656-CRTAC1-cartilage acidic protein 1
15678-CALM2-calmodulin 2 (phosphorylase kinase, delta)
15719-ACOX1-acyl-Coenzyme A oxidase 1, palmitoyl
15753-EEF1E1-eukaryotic translation elongation factor 1 epsilon 1
15799-UXS1-UDP-glucuronate decarboxylase 1
15824-LOC51619-ubiquitin-conjugating enzyme HBUCE1
15864-TGM3-transglutaminase 3 (E polypeptide, protein-glutamine-gamma-glutamyltransferase)
15985-NUCB1-nucleobindin 1
16065-KNTC2-kinetochore associated 2
16118-FCRH1-Fc receptor-like protein 1
16152-SELS-selenoprotein S
16163-USP34-ubiquitin specific protease 34
16196-Oxa1l-oxidase assembly 1-like
16249-NPDC1-neural proliferation, differentiation and control, 1
16299-SLC17A5-solute carrier family 17 (anion/sugar transporter), member 5
16403-APPBP2-amyloid beta precursor protein (cytoplasmic tail) binding protein 2
16538-SLC16A4-solute carrier family 16 (monocarboxylic acid transporters), member 4
16549-ARHGEF6-Rac/Cdc42 guanine nucleotide exchange factor (GEF) 6
16566-TRIM6-tripartite motif-containing 6
16592-ASGR2-asialoglycoprotein receptor 2
16780-CAPS-calcyphosine
16786-CPB1-carboxypeptidase B1 (tissue)
16850-PLXND1-plexin D1
16898-TPD52L1-tumor protein D52-like 1
16918-TUBG1-tubulin, gamma 1

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

16947-HPCA-hippocalcin
16997-CPE-carboxypeptidase E
17216-ARG2-arginase, type II
17304-QPRT-quinolinate phosphoribosyltransferase (nicotinate-nucleotide pyrophosphorylase (carboxylating))
17312-8D6A-8D6 antigen
17349-MGAT4A-mannosyl (alpha-1,3-)-glycoprotein beta-1,4-N-acetylglucosaminyltransferase, isoenzyme A
17352-JFC1-NADPH oxidase-related, C2 domain-containing protein
17426-DAG1-dystroglycan 1 (dystrophin-associated glycoprotein 1)
17464-FLJ30092-AF-1 specific protein phosphatase
17485-RHOA-ras homolog gene family, member A
17608-ZIC4-Zic family member 4
17620-EI24-etoposide induced 2.4 mRNA
17668-PSME2-proteasome (prosome, macropain) activator subunit 2 (PA28 beta)
17745-LHPP-phospholysine phosphohistidine inorganic pyrophosphate phosphatase
17754-PLCG2-phospholipase C, gamma 2 (phosphatidylinositol-specific)
17790-CLEC2-C-type lectin-like receptor-2
17800-P4HB-procollagen-proline, 2-oxoglutarate 4-dioxygenase (proline 4-hydroxylase), beta polypeptide (protein disulfide isomerase; thyroid hormone binding protein p55)
17836-MCAM-melanoma cell adhesion molecule
17862-BBS2-Bardet-Biedl syndrome 2
17882-ATP5F1-ATP synthase, H+ transporting, mitochondrial F0 complex, subunit b, isoform 1
17924-SLC35E1-solute carrier family 35, member E1
17934-NTAN1-N-terminal asparagine amidase
17948-hIAN6-human immune associated nucleotide 6
17971-LOXL1-lysyl oxidase-like 1
18072-MEF2B-MADS box transcription enhancer factor 2, polypeptide B (myocyte enhancer factor 2B)
18162-PTGS1-prostaglandin-endoperoxide synthase 1 (prostaglandin G/H synthase and cyclooxygenase)
18170-RPA3-replication protein A3, 14 kDa
18225-CFL1-cofilin 1 (non-muscle)
18228-FBN1-fibrillin 1 (Marfan syndrome)
18389-SOX7-SRY (sex determining region Y)-box 7
18443-STK35-serine/threonine kinase 35
18464-ZFYVE20-zinc finger, FYVE domain containing 20
18544-PACSIN1-protein kinase C and casein kinase substrate in neurons 1
18565-GNB5-guanine nucleotide binding protein (G protein), beta 5
18594-USP37-ubiquitin specific protease 37
18623-SOX10-SRY (sex determining region Y)-box 10
18648-CL640-hypothetical protein CL640
18686-SET-SET translocation (myeloid leukemia-associated)
18751-MCCC1-methylcrotonoyl-Coenzyme A carboxylase 1 (alpha)
18798-AMT-aminomethyltransferase (glycine cleavage system protein T)
18913-SKP2-S-phase kinase-associated protein 2 (p45)
18916-SERPINE1-serine (or cysteine) proteinase inhibitor, clade E (nexin, plasminogen activator inhibitor type 1), member 1
18950-ACTA2-actin, alpha 2, smooth muscle, aorta
18986-CDC42EP1-CDC42 effector protein (Rho GTPase binding) 1
19008-ECH1-enoyl Coenzyme A hydratase 1, peroxisomal
19191-IGJ-immunoglobulin J polypeptide, linker protein for immunoglobulin alpha and mu polypeptides
19199-FURIN-furin (paired basic amino acid cleaving enzyme)

day 365

00012-ZNF224-zinc finger protein 224
00015-DAPK1-death-associated protein kinase 1
00018-EPHB2-EphB2
00059-PAOX-polyamine oxidase (exo-N4-amino)
00063-PDCD11-programmed cell death 11
00100-NCOA3-nuclear receptor coactivator 3
00248-FMNL1-formin-like 1
00386-SERTAD1-SERTA domain containing 1
00390-GNAS-GNAS complex locus
00393-NOS2A-nitric oxide synthase 2A (inducible, hepatocytes)
00402-SCG2-secretogranin II (chromogranin C)
00408-JRK-jerky homolog (mouse)
00435-MAPT-microtubule-associated protein tau
00436-DGCR14-DiGeorge syndrome critical region gene 14
00549-FY-Duffy blood group
00564-PLCB4-phospholipase C, beta 4
00566-SGK-serum/glucocorticoid regulated kinase
00595-FRAP1-FK506 binding protein 12-rapamycin associated protein 1
00692-MADH3-MAD, mothers against decapentaplegic homolog 3 (*Drosophila*)
00941-COX4I1-cytochrome c oxidase subunit IV isoform 1
00974-DYRK4-dual-specificity tyrosine-(Y)-phosphorylation regulated kinase 4
01042-GAB1-GRB2-associated binding protein 1
01152-KDELR1-KDEL (Lys-Asp-Glu-Leu) endoplasmic reticulum protein retention receptor 1

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

01170-SAT-spermidine/spermine N1-acetyltransferase
01193-RPS28-ribosomal protein S28
01213-TFEB-transcription factor EB
01266-GSN-gelsolin (amyloidosis, Finnish type)
01336-SLC2A4RG-SLC2A4 regulator
01354-KIAA1285-KIAA1285 protein
01418-SULT1A1-sulfotransferase family, cytosolic, 1A, phenol-preferring, member 1
01438-MRPL22-mitochondrial ribosomal protein L22
01463-ELAC1-elaC homolog 1 (*E. coli*)
01521-ASMTL-acetylserotonin O-methyltransferase-like
01527-UBE2A-ubiquitin-conjugating enzyme E2A (RAD6 homolog)
01528-BTBD14B-BTB (POZ) domain containing 14B
01715-RECK-reversion-inducing-cysteine-rich protein with kazal motifs
01757-ICAM3-intercellular adhesion molecule 3
01819-PTPRE-protein tyrosine phosphatase, receptor type, E
01839-MAD-MAX dimerization protein 1
01857-ASB8-ankyrin repeat and SOCS box-containing 8
01888-ANKRD17-ankyrin repeat domain 17
02017-TTN-titin
02027-MAST2-microtubule associated serine/threonine kinase 2
02031-DP1-polyposis locus protein 1
02080-PPHLN1-periphilin 1
02174-HLA-DRB3-major histocompatibility complex, class II, DR beta 3
02175-PCM1-pericentriolar material 1
02225-ASH1L-ash1 (absent, small, or homeotic)-like (*Drosophila*)
02277-DELGEF-deafness locus associated putative guanine nucleotide exchange factor
02358-ITGB4-integrin, beta 4
02393-NRIP1-nuclear receptor interacting protein 1
02485-GEMIN4-gem (nuclear organelle) associated protein 4
02522-TRIM41-tripartite motif-containing 41
02554-RANGAP1-Ran GTPase activating protein 1
02601-SULF2-sulfatase 2
02612-TP53I11-tumor protein p53 inducible protein 11
02615-PFC-properdin P factor, complement
02665-PRSS16-protease, serine, 16 (thymus)
02750-HOXA11-homeo box A11
02752-KDELR1-KDEL (Lys-Asp-Glu-Leu) endoplasmic reticulum protein retention receptor 1
02760-KAI1-kangai 1 (suppression of tumorigenicity 6, prostate; CD82 antigen
(R2 leukocyte antigen, antigen detected by monoclonal and antibody IA4))
02786-ATP5O-ATP synthase, H+ transporting, mitochondrial F1 complex,
O subunit (oligomycin sensitivity conferring protein)
02935-MBD3-methyl-CpG binding domain protein 3
03239-FLJ21128-hypothetical protein FLJ21128
03260-SCYL1-SCY1-like 1 (*S. cerevisiae*)
03262-SEC24A-SEC24 related gene family, member A (*S. cerevisiae*)
03279-MKRN2-makorin, ring finger protein, 2
03394-PIP5K1B-phosphatidylinositol-4-phosphate 5-kinase, type I, beta
03427-SIGIRR-single Ig IL-1R-related molecule
03431-PHCA-phytoceramidase, alkaline
03437-COLQ-collagen-like tail subunit (single strand of homotrimer) of asymmetric acetylcholinesterase
03443-TRIM32-tripartite motif-containing 32
03484-MARS-methionine-tRNA synthetase
03485-BAP1-BRCA1 associated protein-1 (ubiquitin carboxy-terminal hydrolase)
03490-TGFA-transforming growth factor, alpha
03545-SLC30A5-solute carrier family 30 (zinc transporter), member 5
03560-RAI3-retinoic acid induced 3
03586-EPB41L4B-erythrocyte membrane protein band 4.1 like 4B
03590-ZNF75A-zinc finger protein 75a
03678-PNUTL1-peanut-like 1 (*Drosophila*)
03683-RPL31-ribosomal protein L31
03770-ILF3-interleukin enhancer binding factor 3, 90 kDa
03793-MGC5178-hypothetical protein MGC5178
03824-ACTR1A-ARP1 actin-related protein 1 homolog A, centractin alpha (yeast)
03825-RAB13-RAB13, member RAS oncogene family
03865-CLOCK-clock homolog (mouse)
03898-PRDX4-peroxiredoxin 4
03927-ATF6-activating transcription factor 6
03954-CLTB-clathrin, light polypeptide (Lcb)
04006-CKAP4-cytoskeleton-associated protein 4
04045-STAU-staufen, RNA binding protein (*Drosophila*)
04119-AF5Q31-ALL1 fused gene from 5q31
04145-SLC6A1-solute carrier family 6 (neurotransmitter transporter, GABA), member 1
04209-RAB26-RAB26, member RAS oncogene family
04268-H6PD-hexose-6-phosphate dehydrogenase (glucose 1-dehydrogenase)
04556-VPS28-vacuolar protein sorting 28 (yeast)

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

04606-STRN4-striatin, calmodulin binding protein 4
04616-ECM1-extracellular matrix protein 1
04668-FBXL10-F-box and leucine-rich repeat protein 10
04721-ASMTL-acetylserotonin O-methyltransferase-like
04742-NDUFS1-NADH dehydrogenase (ubiquinone) Fe—S protein 1, 75 kDa (NADH-coenzyme Q reductase)
04745-FLJ13352-hypothetical protein FLJ13352
05016-EIF3S4-eukaryotic translation initiation factor 3, subunit 4 delta, 44 kDa
05071-GNA14-guanine nucleotide binding protein (G protein), alpha 14
05093-RPS3A-ribosomal protein S3A
05200-SILV-silver homolog (mouse)
05373-ZFP36L1-zinc finger protein 36, C3H type-like 1
05463-CDW52-CDW52 antigen (CAMPATH-1 antigen)
05553-CDC34-cell division cycle 34
05601-CABIN1-calcineurin binding protein 1
05623-SPOCK2-sparc/osteonectin, cwcv and kazal-like domains proteoglycan (testican) 2
05629-ILF3-interleukin enhancer binding factor 3, 90 kDa
05666-RAD23B-RAD23 homolog B (S. cerevisiae)
05674-CKLF-chemokine-like factor
05680-HIRA-HIR histone cell cycle regulation defective homolog A (S. cerevisiae)
05731-C21orf63-chromosome 21 open reading frame 63
05761-GALT-galactose-1-phosphate uridylyltransferase
05775-GLUL-glutamate-ammonia ligase (glutamine synthase)
05811-FTH1-ferritin, heavy polypeptide 1
05823-FER1L3-fer-1-like 3, myoferlin (C. elegans)
05827-SRP14-signal recognition particle 14 kDa (homologous Alu RNA binding protein)
05889-ERP70-protein disulfide isomerase related protein (calcium-binding protein, intestinal-related)
05897-IL11RA-interleukin 11 receptor, alpha
05936-C10orf9-chromosome 10 open reading frame 9
05943-SHARP-SMART/HDAC1 associated repressor protein
05969-DDX5-DEAD (Asp-Glu-Ala-Asp) box polypeptide 5
05999-NEDD8-neural precursor cell expressed, developmentally down-regulated 8
06080-ATP13A-ATPase type 13A
06092-ZNF384-zinc finger protein 384
06186-RCN3-reticulocalbin 3, EF-hand calcium binding domain
06196-HLA-B-major histocompatibility complex, class I, B
06217-PTGS1-prostaglandin-endoperoxide synthase 1 (prostaglandin G/H synthase and cyclooxygenase)
06257-SUI1-putative translation initiation factor
06277-DustyPK-dusty protein kinase
06286-ZFP36L2-zinc finger protein 36, C3H type-like 2
06320-SF3B2-splicing factor 3b, subunit 2, 145 kDa
06345-LMOD1-leiomodin 1 (smooth muscle)
06466-GTL3-likely ortholog of mouse gene trap locus 3
06497-PGPEP1-pyroglutamyl-peptidase I
06521-COL5A3-collagen, type V, alpha 3
06554-TRAPPC1-trafficking protein particle complex 1
06608-GMNN-geminin, DNA replication inhibitor
06636-NR4A3-nuclear receptor subfamily 4, group A, member 3
06672-RPS3A-ribosomal protein S3A
06726-ZNF219-zinc finger protein 219
06842-TOB2-transducer of ERBB2, 2
06891-LOC57019-hypothetical protein LOC57019
06925-KDELR1-KDEL (Lys-Asp-Glu-Leu) endoplasmic reticulum protein retention receptor 1
07001-DSC2-desmocollin 2
07008-URKL1-uridine kinase-like 1
07018-RPS6-ribosomal protein S6
07119-RPS27L-ribosomal protein S27-like
07129-HLA-DRB3-major histocompatibility complex, class II, DR beta 3
07142-HK3-hexokinase 3 (white cell)
07211-NCOR1-nuclear receptor co-repressor 1
07264-SLC9A5-solute carrier family 9 (sodium/hydrogen exchanger), isoform 5
07274-CKLF-chemokine-like factor
07322-TLE2-transducin-like enhancer of split 2 (E(sp1) homolog, Drosophila)
07344-FLJ23469-hypothetical protein FLJ23469
07346-RAB6A-RAB6A, member RAS oncogene family
07366-CAMKK1-calcium/calmodulin-dependent protein kinase kinase 1, alpha
07469-VIM-vimentin
07496-FMN2-formin 2
07520-ACTR1B-ARP1 actin-related protein 1 homolog B, centractin beta (yeast)
07526-TLE2-transducin-like enhancer of split 2 (E(sp1) homolog, Drosophila)
07602-YWHAQ-tyrosine 3-monooxygenase/tryptophan 5-monooxygenase activation protein, theta polypeptide
07657-PLOD-procollagen-lysine, 2-oxoglutarate 5-dioxygenase (lysine hydroxylase, Ehlers-Danlos syndrome type VI)
07701-GNS-glucosamine (N-acetyl)-6-sulfatase (Sanfilippo disease IIID)
07750-NBL1-neuroblastoma, suppression of tumorigenicity 1
07759-IMMT-inner membrane protein, mitochondrial (mitofilin)

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

07781-CD68-CD68 antigen
07788-DPF2-D4, zinc and double PHD fingers family 2
07789-PPP2R5C-protein phosphatase 2, regulatory subunit B (B56), gamma isoform
07809-SLC9A1-solute carrier family 9 (sodium/hydrogen exchanger), isoform 1 (antiporter, Na+/H+, amiloride sensitive)
07827-ANXA11-annexin A11
07898-IFI30-interferon, gamma-inducible protein 30
07913-C5-complement component 5
07950-SSRP1-structure specific recognition protein 1
08041-NRG1-neuregulin 1
08125-FN1-fibronectin 1
08141-EPB49-erythrocyte membrane protein band 4.9 (dematin)
08150-JAK1-Janus kinase 1 (a protein tyrosine kinase)
08163-IL16-interleukin 16 (lymphocyte chemoattractant factor)
08230-PPP2CB-protein phosphatase 2 (formerly 2A), catalytic subunit, beta isoform
08265-BENE-BENE protein
08272-RPS3A-ribosomal protein S3A
08329-TBXA2R-thromboxane A2 receptor
08343-UBE2V2-ubiquitin-conjugating enzyme E2 variant 2
08417-TAGLN2-transgelin 2
08433-NTRK3-neurotrophic tyrosine kinase, receptor, type 3
08543-FLJ22021-hypothetical protein FLJ22021
08654-DAZAP1-DAZ associated protein 1
08657-RQCD1-RCD1 required for cell differentiation 1 homolog (*S. pombe*)
08692-TA-PP2C-T-cell activation protein phosphatase 2C
08696-ENG-endoglin (Osler-Rendu-Weber syndrome 1)
08747-UBE2V2-ubiquitin-conjugating enzyme E2 variant 2
08786-IL8-interleukin 8
08850-PFN2-profilin 2
08938-GTF3A-general transcription factor IIIA
08942-DNM1-dynamin 1
08974-UAP1-UDP-N-acetylglucosamine pyrophosphorylase 1
09002-GSTA3-glutathione S-transferase A3
09069-VIM-vimentin
09086-RPL41-ribosomal protein L41
09132-RPL31-ribosomal protein L31
09206-MOBP-myelin-associated oligodendrocyte basic protein
09298-USP7-ubiquitin specific protease 7 (herpes virus-associated)
09397-PDE2A-phosphodiesterase 2A, cGMP-stimulated
09429-LASP1-LIM and SH3 protein 1
09599-EGFL3-EGF-like-domain, multiple 3
09641-C16orf40-chromosome 16 open reading frame 40
09760-NDUFS7-NADH dehydrogenase (ubiquinone) Fe—S protein 7, 20 kDa (NADH-coenzyme Q reductase)
09872-SEMA3F-sema domain, immunoglobulin domain (Ig), short basic domain, secreted, (semaphorin) 3F
09887-DPT-dermatopontin
09996-TADA3L-transcriptional adaptor 3 (NGG1 homolog, yeast)-like
09997-MDS028-uncharacterized hematopoietic stem/progenitor cells protein MDS028
10011-DDOST-dolichyl-diphosphooligosaccharide-protein glycosyltransferase
10104-ZNF444-zinc finger protein 444
10170-MGC16943-similar to RIKEN cDNA 4933424N09 gene
10172-RPL23A-ribosomal protein L23a
10177-FY-Duffy blood group
10261-BBS1-Bardet-Biedl syndrome 1
10295-IGFBP6-insulin-like growth factor binding protein 6
10344-ISG20-interferon stimulated gene 20 kDa
10454-PPP2R4-protein phosphatase 2A, regulatory subunit B' (PR 53)
10457-PRKCG-protein kinase C, gamma
10542-SYT5-synaptotagmin V
10597-MCM3AP-MCM3 minichromosome maintenance deficient 3 (*S. cerevisiae*) associated protein
10688-LOC134147-hypothetical protein BC001573
10755-COL18A1-collagen, type XVIII, alpha 1
10832-CAPN10-calpain 10
10850-DRPLA-dentatorubral-pallidoluysian atrophy (atrophin-1)
10853-NBEA-neurobeachin
10874-CARD14-caspase recruitment domain family, member 14
10888-BRD2-bromodomain containing 2
10994-RBM10-RNA binding motif protein 10
11000-DGAT1-diacylglycerol O-acyltransferase homolog 1 (mouse)
11001-C20orf121-chromosome 20 open reading frame 121
11029-DKFZP566E144-small fragment nuclease
11122-PTTG1IP-pituitary tumor-transforming 1 interacting protein
11142-DSIPI-delta sleep inducing peptide, immunoreactor
11202-RGS19-regulator of G-protein signalling 19
11275-C17-cytokine-like protein C17
11276-FOSL1-FOS-like antigen 1

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

11332-FLJ11856-putative G-protein coupled receptor GPCR41
11348-IFITM1-interferon induced transmembrane protein 1 (9-27)
11381-RHOT1-ras homolog gene family, member T1
11451-RPS3A-ribosomal protein S3A
11552-C2orf3-chromosome 2 open reading frame 3
11557-DHRS10-dehydrogenase/reductase (SDR family) member 10
11573-Dnaja4-DnaJ (Hsp40) homolog, subfamily A, member 4
11578-FN1-fibronectin 1
11586-SMARCE1-SWI/SNF related, matrix associated, actin dependent regulator of chromatin, subfamily e, member 1
11605-ALDH2-aldehyde dehydrogenase 2 family (mitochondrial)
11741-RPL41-ribosomal protein L41
11742-CHERP-calcium homeostasis endoplasmic reticulum protein
11777-TUBB4-tubulin, beta, 4
11796-HEL308-DNA helicase HEL308
11824-CSDA-cold shock domain protein A
11826-SNX15-sorting nexin 15
11830-CD44-CD44 antigen (homing function and Indian blood group system)
11880-NR1D1-nuclear receptor subfamily 1, group D, member 1
11925-ZNF606-zinc finger protein 606
11929-EHD2-EH-domain containing 2
12046-DDOST-dolichyl-diphosphooligosaccharide-protein glycosyltransferase
12071-TM4SF8-transmembrane 4 superfamily member 8
12175-FLJ14360-hypothetical protein FLJ14360
12188-TERE1-transitional epithelia response protein
12199-BDH-3-hydroxybutyrate dehydrogenase (heart, mitochondrial)
12204-GSTO1-glutathione S-transferase omega 1
12214-NS-nucleostemin
12225-B3GALT4-UDP-Gal:betaGlcNAc beta 1,3-galactosyltransferase, polypeptide 4
12286-CHAF1A-chromatin assembly factor 1, subunit A (p150)
12288-MLF1-myeloid leukemia factor 1
12378-ARGBP2-Arg/Abl-interacting protein ArgBP2
12425-IMPA2-inositol(myo)-1(or 4)-monophosphatase 2
12426-FNBP2-formin binding protein 2
12503-DDX3X-DEAD (Asp-Glu-Ala-Asp) box polypeptide 3, X-linked
12599-SULT1E1-sulfotransferase family 1E, estrogen-preferring, member 1
12620-HLA-DRB3-major histocompatibility complex, class II, DR beta 3
12625-MCM4-MCM4 minichromosome maintenance deficient 4 (*S. cerevisiae*)
12626-RAB39B-RAB39B, member RAS oncogene family
12720-ATP6V1B2-ATPase, H+ transporting, lysosomal 56/58 kDa, V1 subunit B, isoform 2
12723-GLI4-GLI-Kruppel family member GLI4
12785-DDX48-DEAD (Asp-Glu-Ala-Asp) box polypeptide 48
12859-Cbx5-chromobox homolog 5 (*Drosophila* HP1a)
12881-MKI67IP-MKI67 (FHA domain) interacting nucleolar phosphoprotein
13010-MAT1A-methionine adenosyltransferase I, alpha
13018-CBFA2T3-core-binding factor, runt domain, alpha subunit 2; translocated to, 3
13024-SP100-nuclear antigen Sp100
13094-RPL31-ribosomal protein L31
13204-PIP3-E-phosphoinositide-binding protein PIP3-E
13316-CGA-glycoprotein hormones, alpha polypeptide
13356-HLA-E-major histocompatibility complex, class I, E
13373-KIAA0420-KIAA0420 gene product
13380-CLSTN3-calsyntenin 3
13393-PARG-poly (ADP-ribose) glycohydrolase
13419-GTPBP1-GTP binding protein 1
13423-ESD-esterase D/formylglutathione hydrolase
13547-TRIM29-tripartite motif-containing 29
13562-ACMSD-aminocarboxymuconate semialdehyde decarboxylase
13671-RHCE-Rhesus blood group, CcEe antigens
13718-FXR2-fragile X mental retardation, autosomal homolog 2
13798-KIF12-kinesin family member 12
13837-DUSP1-dual specificity phosphatase 1
13915-REV1L-REV1-like (yeast)
13949-PCSK7-proprotein convertase subtilisin/kexin type 7
13988-WRN-Werner syndrome
14016-MYH10-myosin, heavy polypeptide 10, non-muscle
14018-KIF2-kinesin heavy chain member 2
14042-RBM8A-RNA binding motif protein 8A
14068-IGHMBP2-immunoglobulin mu binding protein 2
14129-TMF1-TATA element modulatory factor 1
14156-PER1-period homolog 1 (*Drosophila*)
14203-ZNF562-zinc finger protein 562
14208-LSS-lanosterol synthase (2,3-oxidosqualene-lanosterol cyclase)
14224-PTK9-PTK9 protein tyrosine kinase 9
14328-COPS8-COP9 constitutive photomorphogenic homolog subunit 8 (Arabidopsis)

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

14429-MGC45419-Similar to calcium/calmodulin-dependent protein kinase 1, beta
14462-WAS-Wiskott-Aldrich syndrome (eczema-thrombocytopenia)
14521-HLA-DQB1-major histocompatibility complex, class II, DQ beta 1
14524-NCOA6IP-nuclear receptor coactivator 6 interacting protein
14529-TCL1A-T-cell leukemia/lymphoma 1A
14536-ZYX-zyxin
14633-DIA1-diaphorase (NADH) (cytochrome b-5 reductase)
14688-EVPL-envoplakin
14798-RPL41-ribosomal protein L41
14826-CASC3-cancer susceptibility candidate 3
14897-BG1-lipidosin
14906-PGR1-T-cell activation protein
14926-CHST5-carbohydrate (N-acetylglucosamine 6-O) sulfotransferase 5
14941-RPS28-ribosomal protein S28
14944-CELSR2-cadherin, EGF LAG seven-pass G-type receptor 2 (flamingo homolog, *Drosophila*)
14952-FXYD5-FXYD domain containing ion transport regulator 5
14957-CCT5-chaperonin containing TCP1, subunit 5 (epsilon)
15023-INHBA-inhibin, beta A (activin A, activin AB alpha polypeptide)
15027-CCND1-cyclin D1 (PRAD1: parathyroid adenomatosis 1)
15028-CIAO1-WD40 protein Ciao1
15180-AKAP8L-A kinase (PRKA) anchor protein 8-like
15229-NUP155-nucleoporin 155 kDa
15235-MDH2-malate dehydrogenase 2, NAD (mitochondrial)
15307-BIRC4-baculoviral IAP repeat-containing 4
15325-DLG5-discs, large homolog 5 (*Drosophila*)
15341-ADORA1-adenosine A1 receptor
15354-GRIN1-glutamate receptor, ionotropic, N-methyl D-aspartate 1
15363-CTSE-cathepsin E
15416-ADD1-adducin 1 (alpha)
15422-PFN2-profilin 2
15435-PLEKHA4-pleckstrin homology domain containing, family A (phosphoinositide binding specific) member 4
15440-SQRDL-sulfide quinone reductase-like (yeast)
15454-CHST5-carbohydrate (N-acetylglucosamine 6-O) sulfotransferase 5
15461-DOK2-docking protein 2, 56 kDa
15488-MGC4083-tubulin beta MGC4083
15562-CDC25B-cell division cycle 25B
15677-SYN1-synapsin I
15699-PES1-pescadillo homolog 1, containing BRCT domain (zebrafish)
15753-EEF1E1-eukaryotic translation elongation factor 1 epsilon 1
15754-ZFP91-zinc finger protein 91 homolog (mouse)
15822-UBA52-ubiquitin A-52 residue ribosomal protein fusion product 1
15824-LOC51619-ubiquitin-conjugating enzyme HBUCE1
15828-FBXO32-F-box only protein 32
15862-SDHB-succinate dehydrogenase complex, subunit B, iron sulfur (Ip)
16074-HLA-DPB1-major histocompatibility complex, class II, DP beta 1
16083-CCNK-cyclin K
16166-RHAG-Rhesus blood group-associated glycoprotein
16350-PSMD3-proteasome (prosome, macropain) 26S subunit, non-ATPase, 3
16399-DNAJB12-DnaJ (Hsp40) homolog, subfamily B, member 12
16469-NFKB1-nuclear factor of kappa light polypeptide gene enhancer in B-cells 1 (p105)
16860-API5-apoptosis inhibitor 5
16872-NOTCH4-Notch homolog 4 (*Drosophila*)
16947-HPCA-hippocalcin
17093-HLA-DRB3-major histocompatibility complex, class II, DR beta 3
17283-FGG-fibrinogen, gamma polypeptide
17426-DAG1-dystroglycan 1 (dystrophin-associated glycoprotein 1)
17496-MSR1-macrophage scavenger receptor 1
17524-TIMP3-tissue inhibitor of metalloproteinase 3 (Sorsby fundus dystrophy, pseudoinflammatory)
17631-TFR2-transferrin receptor 2
17662-SUI1-putative translation initiation factor
17679-RELB-v-rel reticuloendotheliosis viral oncogene homolog B,
nuclear factor of kappa light polypeptide gene enhancer in B-cells 3 (avian)
17936-FADS1-fatty acid desaturase 1
17948-hIAN6-human immune associated nucleotide 6
17963-RAF1-v-raf-1 murine leukemia viral oncogene homolog 1
18072-MEF2B-MADS box transcription enhancer factor 2, polypeptide B (myocyte enhancer factor 2B)
18210-FCGR2B-Fc fragment of IgG, low affinity IIb, receptor for (CD32)
18212-CENPF-centromere protein F, 350/400 ka (mitosin)
18228-FBN1-fibrillin 1 (Marfan syndrome)
18470-KRT13-keratin 13
18482-DLC1-deleted in liver cancer 1
18509-SIAT7D-sialyltransferase 7D ((alpha-N-acetylneuraminyl-2,3-beta-galactosyl-1,3)-
N-acetyl galactosaminide alpha-2,6-sialyltransferase)
18648-CL640-hypothetical protein CL640

TABLE V-continued

Gene sets used to evaluate the correlation between the donor and recipient gene expression profiles. The gene sets include the top 400 genes showing differential expression in GVHD+ vs. GVHD− donors on day 0, combined with the top 400 genes showing differential expression in GVHD+ vs. GVHD− recipients on day 365.

18758-MACF1-microtubule-actin crosslinking factor 1
18761-ch-TOG-KIAA0097 gene product
18850-SNTA1-syntrophin, alpha 1 (dystrophin-associated protein A1, 59 kDa, acidic component)
18851-TRAF2-TNF receptor-associated factor 2
19017-JAZF1-juxtaposed with another zinc finger gene 1
19142-PRKAR2A-protein kinase, cAMP-dependent, regulatory, type II, alpha
19154-TRIAD3-TRIAD3 protein
19171-C1S-complement component 1, s subcomponent
19190-HLA-DRB3-major histocompatibility complex, class II, DR beta 3
19199-FURIN-furin (paired basic amino acid cleaving enzyme)

Although the present invention has been described hereinabove by way of specific embodiments thereof, it can be modified, without departing from the spirit and nature of the subject invention as defined in the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09102981B2). An electronic copy of the "Sequence Listing" will also be available from the USPTO upon request and payment of the fee set forth in 37 CFR 1.19(b)(3).

What is claimed is:

1. A method of treating a subject in need of a bone marrow or hematopoietic cell transplant, said method comprising:
 assessing the risk of a candidate human transplant donor of inducing graft versus host disease (GVHD) in a human transplant recipient by a method comprising:
 (a) measuring the level or amount of a TCIRG1 mRNA in a CD4+ and/or CD8+ T cell sample from said candidate human transplant donor to obtain a candidate gene expression profile by:
  (i) obtaining mRNA from said sample;
  (ii) generating cDNA from the obtained mRNA;
  (iii) amplifying the cDNA encoding TCIRG1; and
  (iv) measuring the level of said cDNA encoding TCIRG1;
 (b) comparing said candidate gene expression profile to a corresponding reference gene expression profile, wherein said reference gene expression profile comprises a reference expression value for a TCIRG1 mRNA, said reference gene expression profile being derived from a comparison of: (i) a GVHD+ expression profile comprising a GVHD+ expression value for a TCIRG1 mRNA derived from a CD4+ and/or CD8+ T cell sample obtained from a human transplant donor known to have induced GVHD in a human transplant recipient with (ii) a GVHD− expression profile comprising a GVHD− expression value for a TCIRG1 mRNA derived from a CD4+ and/or CD8+ T cell sample obtained from a human transplant donor known to have not induced GVHD in a human transplant recipient, whereby said reference expression value is determined as being (A) the level of expression midway between said GVHD+ expression value and said GVHD− expression value-whereby the midway level separates a GVHD+ class comprising said GVHD+ expression value from a GVHD− class comprising said GVHD− expression value; (B) the level of expression between said GVHD+ expression value and said GVHD− expression value defined as separating expression values into GVHD+ and GVHD− classes on the basis of discriminatory analysis; or (C) both (A) and (B);
 (c) assessing risk of said candidate human transplant donor of inducing GVHD in a human transplant recipient in accordance with said comparing step of said candidate gene expression profile with said reference gene expression profile, wherein (i) a candidate expression value within said GVHD− class is indicative that said candidate human transplant donor has a reduced risk of inducing GVHD in a transplant recipient, and (ii) a candidate expression value within said GVHD+ class is indicative that said candidate human transplant donor has an increased risk of inducing GVHD in a transplant recipient; and
 (d) either (i) when said candidate human transplant donor has a reduced risk of inducing GVHD in a transplant recipient, transplanting said subject in need of a bone marrow or hematopoietic cell transplant with a bone marrow or hematopoietic cell transplant from said candidate human transplant donor under a standard or less aggressive anti-rejection treatment regimen; or (ii) when said candidate human transplant donor has an increased risk of inducing GVHD in a transplant recipient, transplanting said subject in need of a bone marrow or hematopoietic cell transplant with (a) a bone marrow or hematopoietic cell transplant from said candidate human transplant donor under an aggressive anti-rejection treatment regimen; or (b) a bone marrow or hematopoietic cell transplant from another candidate human transplant donor.

2. The method of claim 1, wherein said CD4+ and/or CD8+ T cell sample is a CD4+ T cell sample.

3. The method of claim 1, wherein said TCIRG1 mRNA comprises the coding sequence of SEQ ID NO: 119.

4. The method of claim 1, wherein said reference expression value is determined as being (A) the level of expression midway between said GVHD+ expression value and said GVHD− expression value.

5. The method of claim 1, wherein the reference gene expression profile is contained within a database.

6. The method of claim 1, wherein said comparing is carried out using a computer algorithm.

7. The method of claim 1, wherein said candidate gene expression profile further comprises a candidate expression value for a CD24 mRNA, wherein said reference gene expression profile further comprises a reference expression value for said CD24 mRNA, and wherein said method further comprises determining the level or amount of said CD24 mRNA.

8. The method of claim 1, wherein said candidate gene expression profile further comprises a candidate expression value for a PRF1 mRNA, wherein said reference gene expression profile further comprises a reference expression value for said PRF1 mRNA, and wherein said method further comprises determining the level or amount of said PRF1 mRNA.

9. The method of claim 1, wherein said candidate gene expression profile further comprises a candidate expression value for an SH3KBP1 mRNA, wherein said reference gene expression profile further comprises a reference expression value for said SH3KBP1 mRNA, and wherein said method further comprises determining the level or amount of said SH3KBP1 mRNA.

10. The method of claim 1, wherein said candidate gene expression profile further comprises a candidate expression value for an NFAT5 mRNA, wherein said reference gene expression profile further comprises a reference expression value for said NFAT5 mRNA, and wherein said method further comprises determining the level or amount of said NFAT5 mRNA.

11. The method of claim 1, wherein said candidate gene expression profile further comprises a candidate expression value for a CD151 mRNA, wherein said reference gene expression profile further comprises a reference expression value for said CD151 mRNA, and wherein said method further comprises determining the level or amount of said CD151 mRNA.

12. The method of claim 1, wherein said candidate gene expression profile further comprises a candidate expression value for an EP300 mRNA, wherein said reference gene expression profile further comprises a reference expression value for said EP300 mRNA, and wherein said method further comprises determining the level or amount of said EP300 mRNA.

13. The method of claim 1, wherein said candidate gene expression profile further comprises a candidate expression value for a FNBP3 mRNA, wherein said reference gene expression profile further comprises a reference expression value for said FNBP3 mRNA, and wherein said method further comprises determining the level or amount of said FNBP3 mRNA.

14. The method of claim 1, wherein said candidate gene expression profile further comprises a candidate expression value for an NMI mRNA, wherein said reference gene expression profile further comprises a reference expression value for said NMI mRNA, and wherein said method further comprises determining the level or amount of said NMI mRNA.

15. The method of claim 1, wherein said candidate gene expression profile further comprises a candidate expression value for a SIL mRNA, wherein said reference gene expression profile further comprises a reference expression value for said SIL mRNA, and wherein said method further comprises determining the level or amount of said SIL mRNA.

16. The method of claim 1, wherein said candidate gene expression profile further comprises a candidate expression value for a SMAD3 mRNA, wherein said reference gene expression profile further comprises a reference expression value for said SMAD3 mRNA, and wherein said method further comprises determining the level or amount of said SMAD3 mRNA.

17. The method of claim 1, wherein said candidate gene expression profile further comprises a candidate expression value for an AKT2 mRNA, wherein said reference gene expression profile further comprises a reference expression value for said AKT2 mRNA, and wherein said method further comprises determining the level or amount of said AKT2 mRNA.

18. The method of claim 1, wherein said candidate gene expression profile further comprises a candidate expression value for a FURIN mRNA, wherein said reference gene expression profile further comprises a reference expression value for said FURIN mRNA, and wherein said method further comprises determining the level or amount of said FURIN mRNA.

19. The method of claim 1, wherein said candidate gene expression profile further comprises a candidate expression value for an ATBF1 mRNA, wherein said reference gene expression profile further comprises a reference expression value for said ATBF1 mRNA, and wherein said method further comprises determining the level or amount of said ATBF1 mRNA.

20. The method of claim 1, wherein said candidate gene expression profile further comprises a candidate expression value for a TGIF mRNA, wherein said reference gene expression profile further comprises a reference expression value for said TGIF mRNA, and wherein said method further comprises determining the level or amount of said TGIF mRNA.

21. The method of claim 1, wherein said candidate gene expression profile further comprises a candidate expression value for a TGFBI mRNA, wherein said reference gene expression profile further comprises a reference expression value for said TGFBI mRNA, and wherein said method further comprises determining the level or amount of said TGFBI mRNA.

* * * * *